United States Patent
Hatle et al.

(10) Patent No.: US 10,479,113 B1
(45) Date of Patent: Nov. 19, 2019

(54) METHODS, SYSTEMS, AND APPARATUSES FOR DETECTING A MEDIA JAM CONDITION

(71) Applicant: Datamax-O'Neil Corporation, Altamonte Springs, FL (US)

(72) Inventors: Richard Hatle, Casselberry, FL (US); Ronald Schwallie, Lake Mary, FL (US); Jose Fernando Sanchez Gutierrez, Orlando, FL (US)

(73) Assignee: DATAMAX-O'NEIL CORPORATION, Altamonte Springs, FL (US)

( * ) Notice: Subject to any disclaimer, the term of this patent is extended or adjusted under 35 U.S.C. 154(b) by 0 days.

(21) Appl. No.: 16/034,158

(22) Filed: Jul. 12, 2018

(51) Int. Cl.
| | | |
|---|---|---|
| *B41J 11/00* | (2006.01) | |
| *B41J 2/32* | (2006.01) | |
| *B41J 11/48* | (2006.01) | |
| *B41J 29/393* | (2006.01) | |
| *G01N 21/89* | (2006.01) | |
| *G01N 21/86* | (2006.01) | |

(52) U.S. Cl.
CPC .............. *B41J 11/006* (2013.01); *B41J 2/32* (2013.01); *B41J 11/009* (2013.01); *B41J 11/0095* (2013.01); *B41J 11/485* (2013.01); *B41J 29/393* (2013.01); *G01N 21/86* (2013.01); *G01N 21/89* (2013.01); *G01N 2021/8917* (2013.01)

(58) Field of Classification Search
CPC ...... B41J 11/006; B41J 11/485; B41J 29/393; B41J 11/0095; B41J 11/009; B41J 2/32; G01N 2021/8917; G01N 21/86; G01N 21/89

USPC .......................................................... 347/218
See application file for complete search history.

(56) References Cited

U.S. PATENT DOCUMENTS

| | | |
|---|---|---|
| 4,505,572 A | 3/1985 | Ashida et al. |
| 5,105,078 A | 4/1992 | Nochise et al. |
| 5,574,527 A | 11/1996 | Folkins et al. |
| 5,879,092 A * | 3/1999 | Brannan ................. B41J 11/00 400/611 |
| 7,275,009 B2 | 9/2007 | Yasukawa et al. |
| 2006/0221171 A1 * | 10/2006 | Watanabe ................. B41J 2/32 347/215 |

* cited by examiner

*Primary Examiner* — Huan H Tran
*Assistant Examiner* — Alexander D Shenderov
(74) *Attorney, Agent, or Firm* — Alston & Bird LLP

(57) ABSTRACT

The disclosed embodiments illustrate a thermal printer apparatus that includes a media sensor. The sensor generates an input signal indicative of a measure of a media transmissivity/reflectivity. Further, the thermal printer includes a processor that is configured to receive the input signal from the sensor, while the media is stationary with respect to a print head. The processor further determines one or more characteristics of the input signal. Thereafter, a first transmissivity/reflectivity threshold is determined based on the one or more characteristics in the input signal. Further, the processor receives the input signal from the sensor, while the media traverses with respect to the print head. Subsequently, the processor determines one or more current characteristics of the input signal while the media traverses with respect to the print head. A media jam condition is detected based on the one or more current characteristics and the first transmissivity/reflectivity threshold.

22 Claims, 14 Drawing Sheets

METHODS, SYSTEMS, AND APPARATUSES FOR DETECTING A MEDIA JAM CONDITION

TECHNOLOGICAL FIELD

Exemplary embodiments of the present disclosure relate generally to printers and, more particularly, to methods, systems, and apparatuses that detect a media jam condition in printers.

BACKGROUND

Printing systems, such as copiers, printers, facsimile devices or other systems, may be capable of reproducing content, visual images, graphics, texts, etc. on a page or a media. Some examples of the printing systems may include, but not limited to, thermal printers, inkjet printers, laser printers, and/or the like.

A typical thermal printer includes a thermal print head that has one or more heating elements. These heating elements may be individually or collectively energized to perform the printing operation. Examples of the thermal printers may include thermal transfer printers and direct thermal printers. Typically, in thermal transfer printer, content is printed on the media by heating a coating of a ribbon so that the coating is transferred to the media. It contrasts with the direct thermal printing where no ribbon is present in the process.

Typically, in thermal printers, the media is supplied to the print head by means of one or more spindles or a media hanger. However, due to certain reasons, such as obstruction in the media path, and misalignment of the media, a media jam may occur in the thermal printers. Typically, the thermal printer may detect such media jam based on detection of a gap or a label mark on the media. If the gap or the label mark is not detected within a predetermined time period, a media jam is detected. However, until the predetermined time period expires, the spindle keeps supplying the media, which may lead to a messy jam.

Applicant has identified a number of deficiencies and problems associated with conventional methods for detecting media jam condition. Through applied effort, ingenuity, and innovation, many of these identified problems have been solved by developing solutions that are included in embodiments of the present disclosure, many examples of which are described in detail herein.

SUMMARY

Various embodiments illustrated herein disclose a method for detecting a media jam condition in a thermal printer. The method comprises receiving, by a processor, an input signal from a media sensor. The input signal is indicative of a measure of a media transmissivity/reflectivity. Further, the method includes operating, by the processor, the thermal printer in a calibration mode. Operating the thermal printer in the calibration mode comprises halting, by the processor, a traversal of the media such that the media is stationary with respect to a print head in the thermal printer. Further, operating the thermal printer in the calibration mode comprises analyzing, by the processor, the input signal received while the traversal of the media is halted, to determine one or more characteristics of the input signal. Furthermore, operating the thermal printer in the calibration mode comprises determining, by the processor, a first transmissivity/reflectivity threshold based on the one or more characteristics of the input signal received during the calibration mode. Additionally, the method comprises operating, by the processor, the thermal printer in a printing mode. Operating the thermal printer in the printing mode comprises causing, by the processor, traversal of the media with respect to the print head in the thermal printer to perform a print operation. Further, operating the thermal printer in the printing mode comprises determining, by the processor, one or more current characteristics of the input signal received while the thermal printer operates in the printing mode. Finally, operating the thermal printer in the printing mode comprises detecting, by the processor, the media jam condition in an instance in which a measure of the one or more current characteristics of the input signal, received while the thermal printer operates in the printing mode, is satisfies the first transmissivity/reflectivity threshold.

Various embodiments illustrated herein disclose a thermal printer apparatus that includes a media sensor. The media sensor generates an input signal indicative of a measure of a media transmissivity/reflectivity. Further, the thermal printer includes a processor that is configured to receive the input signal from the sensor, while the media is stationary with respect to a print head. The processor further analyzes the input signal, received while the traversal of the media is halted, to determine one or more characteristics of the input signal. Thereafter, a first transmissivity/reflectivity threshold is determined based on the one or more characteristics in the input signal. Further, the processor receives the input signal from the sensor, while the media traverses with respect to the print head. Subsequently, the processor determines one or more current characteristics of the input signal while the media traverses with respect to the print head. A media jam condition is detected based on the one or more current characteristics and the first transmissivity/reflectivity threshold.

Various embodiments illustrated herein disclose a method for detecting a media jam condition in a thermal printer. The method includes receiving, by a processor, an input signal from a media sensor. The input signal is indicative of a measure of a media transmissivity/reflectivity of a media, wherein content is printed on the media. Further, the method includes determining, by the processor, a first transmissivity/reflectivity threshold based on the input signal. Furthermore, the method includes operating, by the processor, the thermal printer in a printing mode. Operating the thermal printer in the printing mode comprises causing, by the processor, traversal of the media with respect to the print head in the thermal printer to perform a print operation. Further, operating the thermal printer in the printing mode comprises determining, by the processor, one or more current characteristics of the input signal received while the thermal printer operates in the printing mode. Additionally, operating the thermal printer in the printing mode comprises detecting, by the processor, the media jam condition in an instance in which a measure of the one or more current characteristics of the input signal, received while the thermal printer operates in the printing mode, is satisfies the first transmissivity/reflectivity threshold.

The above summary is provided merely for purposes of providing an overview of one or more exemplary embodiments described herein so as to provide a basic understanding of some aspects of the disclosure. Accordingly, it will be appreciated that the above-described embodiments are merely examples and should not be construed to narrow the scope or spirit of the disclosure in any way. It will be appreciated that the scope of the disclosure encompasses many potential embodiments in addition to those here summarized, some of which are further explained within the following detailed description and its accompanying drawings.

BRIEF DESCRIPTION OF THE DRAWINGS

The description of the illustrative embodiments can be read in conjunction with the accompanying figures. It will be appreciated that for simplicity and clarity of illustration, elements illustrated in the figures have not necessarily been drawn to scale. For example, the dimensions of some of the elements are exaggerated relative to other elements. Embodiments incorporating teachings of the present disclosure are shown and described with respect to the figures presented herein, in which.

DETAILED DESCRIPTION

Figure 1A:
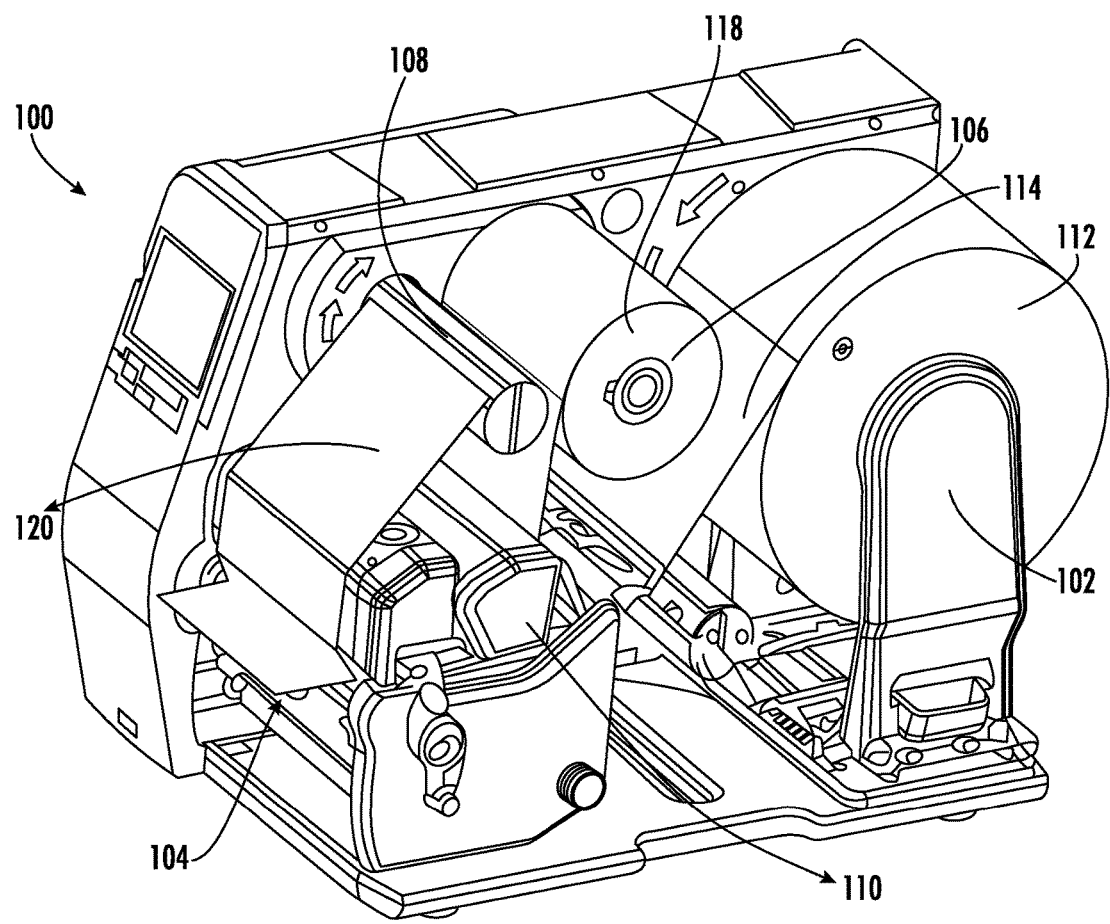
FIGS. 1A, 1B, and 1C illustrate a perspective view of a printer, according to one or more embodiments described herein.

Some embodiments of the present disclosure will now be described more fully hereinafter with reference to the accompanying drawings, in which some, but not all embodiments of the disclosure are shown. Indeed, these disclosures may be embodied in many different forms and should not be construed as limited to the embodiments set forth herein; rather, these embodiments are provided so that this disclosure will satisfy applicable legal requirements. Like numbers refer to like elements throughout. Terminology used in this patent is not meant to be limiting insofar as devices described herein, or portions thereof, may be attached or utilized in other orientations The term "comprising" means including but not limited to, and should be interpreted in the manner it is typically used in the patent context. Use of broader terms such as comprises, includes, and having should be understood to provide support for narrower terms such as consisting of, consisting essentially of, and comprised substantially of.

The phrases "in one embodiment," "according to one embodiment," and the like generally mean that the particular feature, structure, or characteristic following the phrase may be included in at least one embodiment of the present disclosure, and may be included in more than one embodiment of the present disclosure (importantly, such phrases do not necessarily refer to the same embodiment)

The word "exemplary" is used herein to mean "serving as an example, instance, or illustration." Any implementation described herein as "exemplary" is not necessarily to be construed as preferred or advantageous over other implementations.

If the specification states a component or feature "may," "can," "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiments, or it may be excluded.

The word "media" is used herein to mean a printable medium, such as a page or paper, on which content, such as graphics, text, and/or visual images, may be printable. In some embodiments, the media may correspond to a thermal media on which the content is printed on application of heat on the media itself or the media may correspond to a liner media, a liner-less media, and/or the like. The media may correspond to a continuous media that may be loaded in the printer in form of a roll or a stack or may correspond to media that may be divided into one or more portions through perforations defined along a width of the media. Alternatively or additionally, the media may be divided into the one or more portions through one or more marks that are defined at a predetermined distance from each other, along the length of the media. In some example embodiments, a contiguous stretch of the media, between two consecutive marks or two consecutive perforations, corresponds to a portion of the media.

In printers, such as a thermal printer, media (on which the content is to be printed) is supplied to the print head to perform the print operation. After performing the print operation, the printed media is output from an output slot in the printer. Providing the media to the print head and further outputting the printed media from the output slot, requires the media to be traversed along a media path defined in the printer. In certain scenarios, due to obstruction in the media path, and misalignment of the media, a media jam may occur in the printer. Typically, such a media jam is detected by detecting perforations and/or marks on the media. If perforations and/or marks are not detected within a predetermined time period, a media jam is detected. However, until the predetermined time period expires, the media keeps moving along the media path, which in some instances, leads to a messy jam.

Example embodiments described herein illustrate methods of detecting a media jam condition based on an input signal generated by a media sensor in a printer, such as a thermal printer. In some embodiments, the media sensor is utilized to detect a presence of media in the printer. In an example embodiment, the media sensor generates the input signal, indicative of transmissivity/reflectivity of the media, upon which the presence/absence of media may be detected.

To utilize the input signal (generated in some examples by the media sensor) to detect the media jam condition, the processor may be configured to operate the printer in a calibration mode. In the calibration mode, the processor may, in some examples, determine a first transmissivity/reflectivity threshold and a second first transmissivity/reflectivity threshold based on one or more characteristics of the input signal. In some embodiments, the one or more characteristics of the input signal may include, but is not limited to, an amplitude of the input signal and a frequency of the input signal.

In an example embodiment, the processor determines the first transmissivity/reflectivity threshold by analyzing the input signal, received from the media sensor while the media is stationary i.e., the media is not traversing along the media path. When the media is not traversing along the media path, the input signal so generated has a constant or substantially constant amplitude and frequency.

In some examples, due to noisy environment around the media sensor, the input signal may depict some variations in the amplitude and the frequency. In such cases, the processor is configured to analyze these variations in the amplitude and the frequencies to determine the first transmissivity/reflectivity threshold. For example, the processor may be configured to determine a maximum value of the amplitude that the input signal reaches while the media is stationary. Thereafter, the processor may consider the maximum value of the amplitude as the first transmissivity/reflectivity threshold. Alternatively or additionally, the processor may determine a maximum frequency that the input signal reaches while the media is stationary. Thereafter, the processor may consider the maximum value of the frequency as the first transmissivity/reflectivity threshold. In yet another embodiment, the processor may consider the combination of the maximum value of frequency and maximum value of amplitude as the first transmissivity/reflectivity threshold. In yet another embodiment, to determine the transmissivity/reflectivity threshold, the processor may be configured to determine a variation in the amplitude of the input signal, while the media is stationary. In one example where the media is stationary, the processor may be configured to subtract a current value of the amplitude from a chronologically previous value of the amplitude to determine a first variation measure of the amplitude. Thereafter, in some examples, the processor may be configured to determine the first variation measure, as the first transmissivity/reflectivity threshold.

In some embodiments, after determining the first transmissivity/reflectivity threshold, the processor may cause the media to traverse along the media path. While the media traverses along the media path and various points on the media passes over the media sensor, the processor may receive the input signal from the media sensor. Therefore, the one or more characteristics of the input signal may vary indicating the variation in the transmissivity/reflectivity of the media at the various points. For example, the amplitude of the input signal may vary, indicating the variation in the transmissivity/reflectivity of the media at the various points. In an example embodiment, the processor may be configured to analyze these variations in the amplitude and frequencies to determine a second transmissivity/reflectivity threshold. For example, the processor may be configured to determine a maximum value of the amplitude that the input signal reaches while the media traverses along the media path. Thereafter, the processor may consider the maximum value of the amplitude as the second transmissivity/reflectivity threshold. Alternatively or additionally, the processor may determine a maximum frequency that the input signal reaches while the media is traverses along the media path. Thereafter, the processor may consider the maximum value of the frequency as the second transmissivity/reflectivity threshold. In yet another embodiment, the processor may consider the combination of the maximum value of frequency and maximum value of amplitude as the second transmissivity/reflectivity threshold. In yet another embodiment, to determine the second transmissivity/reflectivity threshold, the processor may be configured to determine the variation in the amplitude of the input signal (received from the media sensor) while the media traverses along the media path. In one example where the media traverses along the media path, the processor may be configured to subtract the current value of the amplitude from the chronologically previous value of the amplitude to determine a second variation measure of the amplitude of the input. Further, the processor may be configured to consider the determined second variation measure of the amplitude of the input signal as the second transmissivity/reflectivity threshold.

Additionally or alternately, the processor may determine the first transmissivity/reflectivity threshold while the printer operates in an idle mode. In the idle mode, the printer does not perform a print or calibration operation. For example, when the printer is yet to receive a command to perform the print operation, the printer is said to operate in the idle mode. In some examples, when the printer operates in the idle mode, the media is stationary (i.e., the media does not traverse along the media path). Therefore, the processor may be able to determine the first transmissivity/reflectivity threshold while the printer operates in the idle mode. After determining the first transmissivity/reflectivity threshold and the second transmissivity/reflectivity threshold, the processor may, in some examples, operate the printer in a printing mode. In the printing mode, the printer may receive a print job that, when executed, causes the media to traverse long the media path such that the contents of the print job are burned or otherwise transferred to the media.

During traversal of the media, the processor receives may also receive the input signal from the media sensor. In some examples, the processor determines one or more current characteristics of the input signal (received while the media traverses along the media path). The one or more current characteristics include a current amplitude of the input signal and/or a current frequency of the input signal.

In some example embodiments, the processor determines whether the one or more current characteristics of the input signal satisfy the first transmissivity/reflectivity threshold. For example, in an instance in which the first transmissivity/reflectivity threshold corresponds to a maximum amplitude of the input signal, while the media is stationary, the processor, in some examples, determines whether the current amplitude of the input signal is less than or equal to the maximum amplitude. If the processor determines that the current amplitude is less than or equal to the maximum amplitude, the processor, in some examples, determines that media is jammed and therefore detects the media jam condition. In another example, in an instance in which the first transmissivity/reflectivity threshold corresponds to a maximum frequency, while the media is stationary, the processor, in some examples, determines whether the current frequency of the input signal is greater than or equal to the maximum frequency. If the processor determines that the current frequency is greater than or equal to the maximum frequency, the processor, in some examples, determines that media is jammed and therefore detects the media jam condition. In yet another example, in an instance in which the first transmissivity/reflectivity threshold corresponds to the first variation measure in the amplitude of the input signal, the processor may be configured to determine a current variation measure in the amplitude of the input signal that is received while the printer operates in the printing mode. If the processor determines that the current variation measure of the amplitude of the input signal, received while the printer operates in the printing mode, is less than or equal to the first variation measure (i.e., the first transmissivity/reflectivity threshold), the processor may detect the media jam condition.

Alternatively or additionally, the processor may further perform a check to determine whether the current amplitude of the input signal is less than the maximum amplitude for a predetermined time period or, in some examples, whether the processor has detected that the input signal is less than the maximum amplitude for a predetermined number of steps/counts. If the current amplitude of the input signal is less than the maximum amplitude for the predetermined time period or the predetermined number of steps/counts, only then the processor detects the media jam condition. In some examples, analyzing the current amplitude for the predetermined time period or the predetermined number of steps/counts avoids a false positive detection of the media jam condition.

Figure 1B:
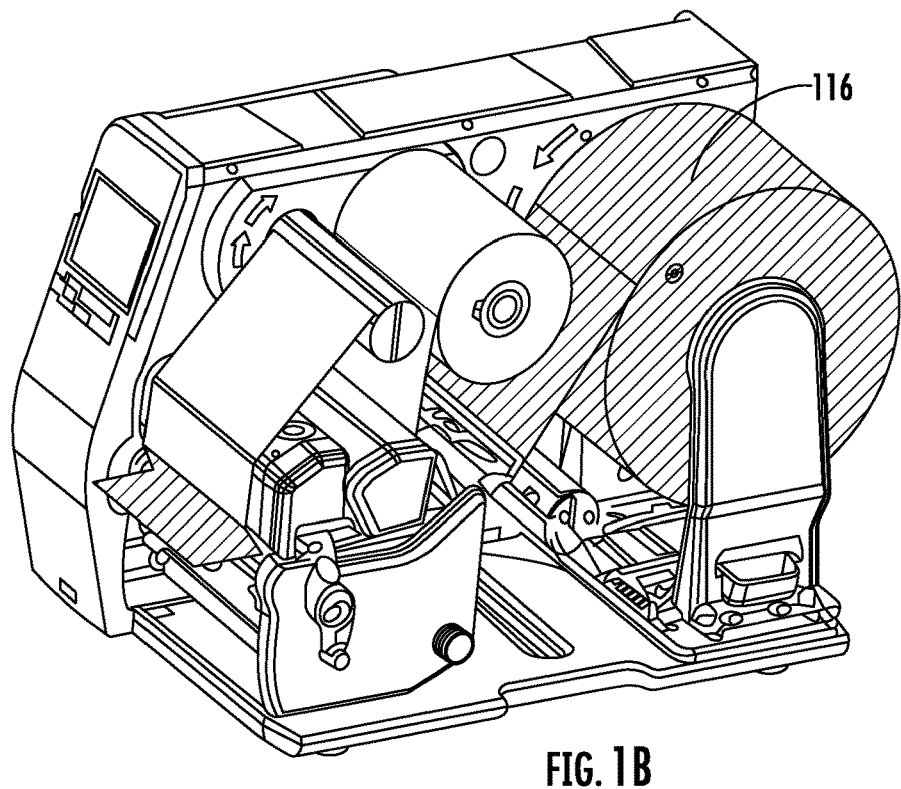
Figure 1C:
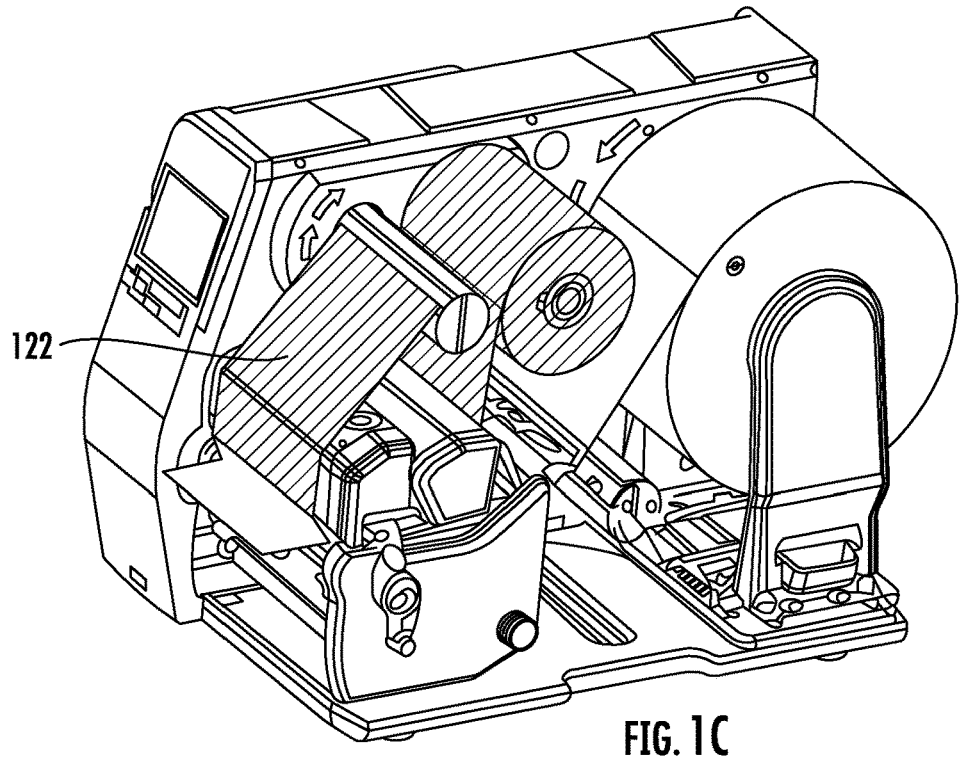

FIGS. 1A, 1B, and 1C illustrate a perspective view of a printer 100, according to one or more embodiments described herein. The printer 100 may include a media hub 102, a printer media output 104, a ribbon drive assembly 106, a ribbon take-up hub 108, and a print head 110.

In an example embodiment, the media hub 102 is configured to receive a media roll 112. In an example embodiment, the media roll 112 may correspond to a roll of a media 114 that may be a continuous media or may, in some example embodiments, include one or more portions that are defined (in the media 114) by means of perforations or one or more marks. In an example embodiment, the media hub 102 is coupled to a first electrical drive (not shown) that actuates the media hub 102. In some examples, the first electrical drive may correspond to a stepper motor that may be configured to move by at least one step on actuation. In an example embodiment, the step of the stepper motor may correspond to a minimum angle by which the stepper motor rotates on actuation.

Actuation of the first electrical drive causes the media hub 102 rotate which causes the media roll 112 to rotate, which further causes the media roll 112 to supply the media 114 to the print head 110 along a media path 116 (shaded in FIG. 1B). In an example embodiment, along the media path 116, the media 114 traverses from the media roll 112 through the print head 110 to the printer media output 104.

In an example embodiment, the printer media output 104 corresponds to a slot through which the printed media is outputted. The width of the printer media output 104 is in accordance with a width of the media 114. In some examples, the width of the printer media output 104 may correspond to a maximum width of the media 114 supported by the printer 100.

The ribbon drive assembly 106 may receive a ribbon roll 118 that corresponds to a roll of a ribbon 120. In an example embodiment, the ribbon 120 may correspond to an ink media that is utilized to dispose ink onto the media 114 to print content on the media 114. In an example embodiment, the ribbon drive assembly 106 may be coupled to a second electrical drive that may be configured to actuate the ribbon drive assembly 106. In some examples, the second electrical drive may also correspond to a stepper motor. On actuation of the ribbon drive assembly 106, the ribbon drive assembly 106 rotates, which in turn causes the ribbon roll to rotate that causes the ribbon roll 118 to supply the ribbon 120 along a ribbon path 122 (shaded in FIG. 1C). Along the ribbon path 122, the ribbon 120 traverses from the ribbon roll 118 to the print head 110 and further to the ribbon take-up hub 108.

In an example embodiment, the ribbon take-up hub 108 may correspond to an assembly that may receive used ribbon (i.e., a section of the ribbon 120 from which the ink has been is disposed on the media 114). The ribbon take-up hub 108 may also be coupled to a third electrical drive (e.g., stepper motor) that may be configured to actuate the ribbon take-up hub 108. On actuation, the ribbon take-up hub 108 pulls the ribbon 120 from the ribbon roll 118. In some examples, the second electrical drive and the third electrical drive may operate in synchronization such that an amount of ribbon 120 released by the ribbon roll 118 (due to actuation of the second electrical drive) is equal to the amount of ribbon 120 received by the ribbon take-up hub 108.

The print head 110 may correspond to a component that is configured to print the content on the media 114. In an example embodiment, the print head 110 may include a plurality of heating elements (not shown) that are energized and pressed against the ribbon 120 to perform a print operation. In operation, the print head 110 applies heat on a portion of the ribbon 120 and, concurrently, presses the ribbon 120 against the media 114 to transfer the ink on the media 114. In an example scenario where the media 114 corresponds to thermal paper, the print head 110 may be directly press against the thermal paper to perform the print operation.

During the print operation, one or more heating elements of the plurality of heating elements are energized to perform the print operation. The one or more heating elements may be selected based on the data in a print job. For example, if a letter "A" is to be printed, the one or more heating elements that are energized are positioned on the print head 110 in such a manner that when the print head 110 is pressed against the ribbon 120 and the media 114, letter "A" gets printed on the media 114. To press the ribbon 120 against the media 114, the print head 110 translates in a vertically downward direction (or downward direction) to push the ribbon 120 against the media 114.

In an example embodiment, after the print operation, the media 114 and the ribbon 120 traverse along the media path 116 and the ribbon path 122, respectively, such that the printed media is outputted from the printer media output 104 and the used ribbon traverses to the ribbon take-up hub 108.

In an example embodiment, the printer 100 may be configured to operate in one or more modes. The one or more modes may include, but are not limited to, a printing mode, a calibration mode, and an idle mode. In the printing mode, the printer 100 is configured to perform the print operation, which is further described in conjunction with FIG. 11. In the calibration mode, the printer 100 is configured to calibrate itself, which is further described in conjunction with FIG. 6. In the idle mode, the printer 100 does not perform any print operation. For example, when the printer 100 is yet to receive a command to perform the print operation, the printer 100 is said to operate in the idle mode. The operation of the printer 100 in the idle mode has been described with reference to FIG. 9.

Figure 2:
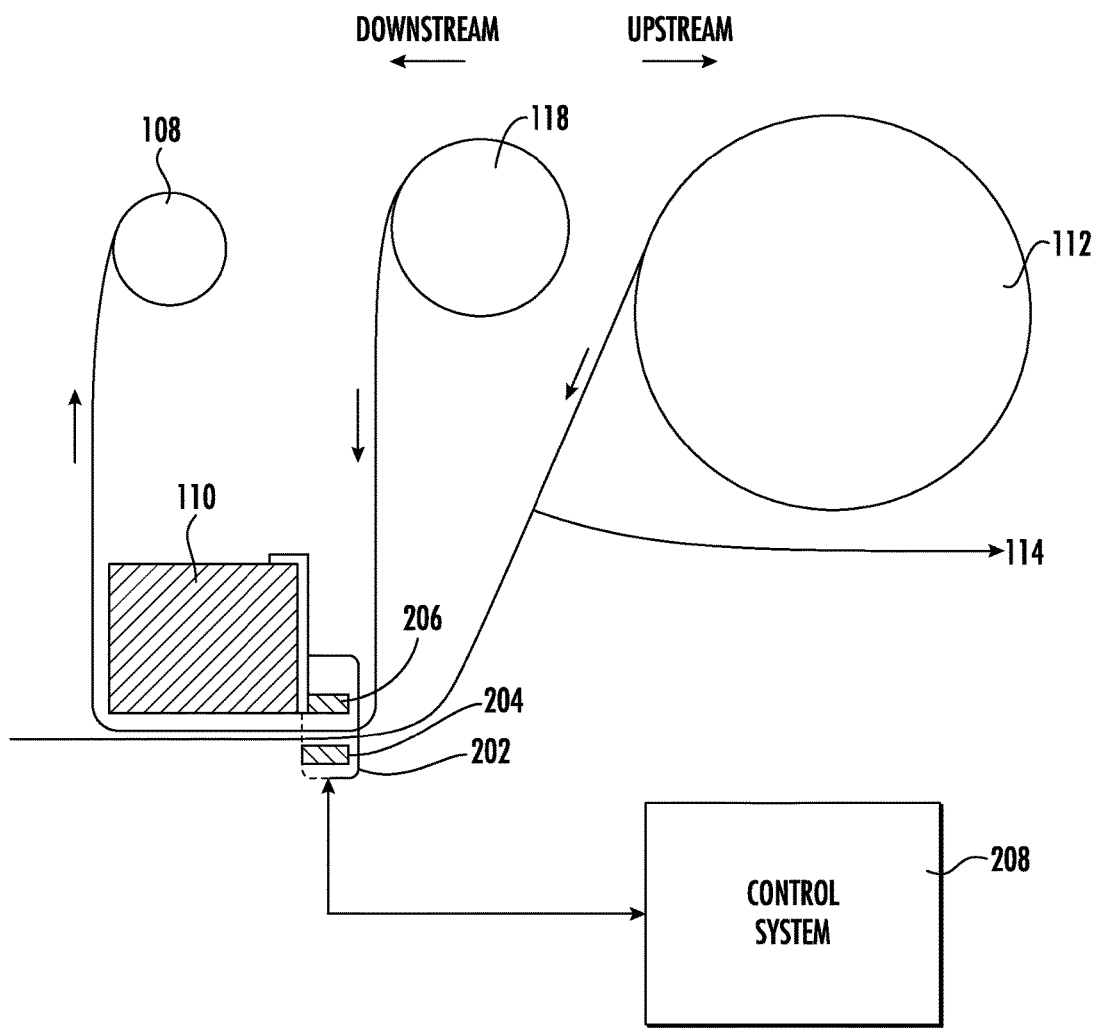
FIG. 2 illustrates a schematic of the printer, according to one or more embodiments described herein.

FIG. 2 illustrates a schematic of the printer 100, according to one or more embodiments described herein. The schematic of the printer 100 illustrates that the printer 100 further includes a media sensor 202 and a control system 208. The schematic of the printer 100 further depicts the media path 116, and the ribbon path 122. Furthermore, the schematic of the printer 100 depicts that the print head 110 is positioned downstream of the media roll 112 along the media path 116, and downstream of the ribbon roll 118 along the ribbon path 122.

In an example embodiment, the print head 110 is positioned on top of both the ribbon path 122 and the media path 116. Further, the ribbon path 122 is proximate to the print head 110 in comparison to the media path 116. Therefore, the ribbon 120 is proximate to the print head 110, in comparison to the media 114, and is therefore, positioned above the media 114. During the print operation, the print head 110 moves in a vertically downward direction to press the ribbon 120 against the media 114 to perform the print operation.

The media sensor 202 may correspond to a sensor that is configured to detect a presence of the media 114 on the media path 116. In some example embodiments, the media sensor 202 may be configured to detect the presence of the media 114 by determining transmissivity and/or reflectivity of the media 114. In an example embodiment, the transmissivity of the media 114 may correspond to a measure of an intensity of a light signal that media 114 allows to pass through it. In an example embodiment, the reflectivity of the media 114 may corresponds to a measure of an intensity of light signal that gets reflected from a surface of the media 114.

In some example embodiments, the media sensor 202 includes a light transmitter 204 and a light receiver 206. The light transmitter 204 that may correspond to a light source, such as a Light Emitting Diode (LED), a LASER, and/or the like. The light transmitter 204 may be configured to direct the light signal on the media path 116. The light receiver 206 may correspond to at least one of a photodetector, a photodiode, or a photo resistor. The light receiver 206 may generate an input signal based on an intensity of the light signal received by the light receiver 206. In an example embodiment, the input signal may correspond to a voltage signal, where the one or more characteristics of the voltage signal, such as the amplitude of the voltage signal and frequency of the voltage signal, are directly proportional to the intensity of the portion of the light signal received by the media sensor 202.

In operation, the light transmitter 204 of the media sensor 202, may be configured to direct the light signal on the media path 116. If the media 114 is present on the media path 116, a portion of light signal may get reflected from the surface of the media 114. The light receiver 206 may receive the portion of the light signal and based on the intensity of the portion of the light signal, the light receiver is configured to generate the input signal based on a measurement of the light signal received. As the intensity of the portion of the light signal reflected from the surface of the media 114 is dependent on the reflectivity of the media 114, the input signal generated by the media sensor 202 (based on the intensity of the portion of the light signal) is indicative of a measure of the reflectivity of the media 114.

Additionally or alternatively, the media sensor 202 may be configured to determine the transmissivity of the media 114. To determine the transmissivity of the media 114, the light receiver 206 may receive the portion of the light signal that passes through the media 114. To receive the portion of the light signal that passes through the media 114, the light receiver 206 is spaced apart from the light transmitter 204 in such a manner that the media 114 passes through a space between the light receiver 206 and the light transmitter 204. When the light transmitter 204 directs the light signal on the media 114, the portion of the light signal passes through the media 114 is receivable by the light receiver 206. The light receiver 206, thereafter may generate the input signal in accordance with the measured intensity of the portion of light signal received. As the intensity of the portion of the light signal that passes through the media 114 is dependent on the transmissivity of the media 114, the input signal generated by the media sensor 202 (based on the intensity of the portion of the light signal) is indicative of a measurement of the transmissivity of the media 114.

In some examples, the media sensor 202 is configured to generate the input signal in accordance with a predetermined sampling rate associated with the media sensor 202. In an example embodiment, the sampling rate may correspond to a frequency at which the media sensor 202 determines the transmissivity/reflectivity of the media 114 and accordingly transmits the input signal. In some examples, the sampling rate of the media sensor 202 may be dependent on a number of steps by which the first electrical drive (coupled to the media hub 102) has moved. For example, if the first electrical drive has moved by 10 steps, the media sensor 202 may be configured to determine transmissivity/reflectivity of the media at each step. Therefore, after the movement of the first electrical drive is complete (e.g., 10 steps), the media sensor 202 may have measured the transmissivity/reflectivity of the media 10 times.

In some embodiments, the media sensor 202 may be utilized to detect the one or more portions of the media 114. As discussed supra, the media 114 may include the one or more portions that are separated either by perforations or by the one or more marks. Therefore, when such marks/perforations on the media 114 passes over the media sensor 202 during traversal of the media 114, the media sensor 202 may detect a sudden increase/decrease in the measure of transmissivity/reflectivity of media 114. Such a sudden increase/decrease in the measure of the transmissivity/reflectivity of media 114, is then reflected in the input signal generated by the media sensor 202. For example, the input signal generated by the media sensor 202 may include spikes or valleys indicating a sudden increase or decrease in the measure of the transmissivity/reflectivity of media 114. Such spikes and valleys may be utilized to identify the one or more portions of the media 114.

The printer 100 further includes a control system 208 that includes suitable logic and circuitry to control the operation of the printer 100. For example, the control system 208 may be configured to control the operation of one or more components of the printer 100, in order to control the operation of the printer 100. For example, the control system 208 may be configured to control the heating/energization of the plurality of heating elements in the print head 110 to execute the print job. Further, the control system 208 may be configured to communicate with the media sensor 202. For example, the control system 208 may be configured to receive the input signal from the media sensor 202. The structure of the control system 208 is further described in conjunction with FIG. 4.

Figure 3A:
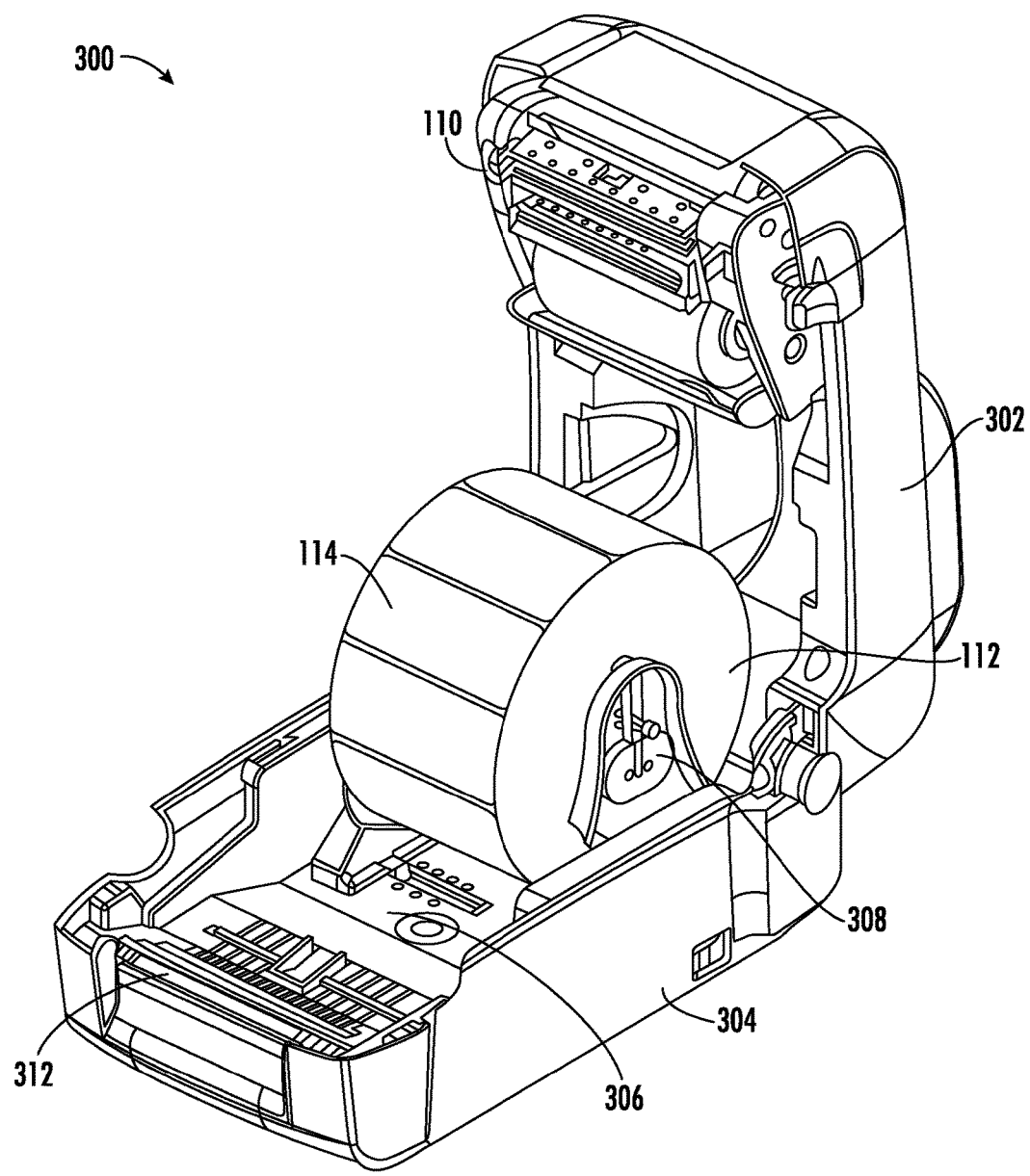
FIGS. 3A and 3B illustrate a perspective view and a schematic of an example direct thermal printer, respectively, according to one or more embodiments described herein.
Figure 3B:
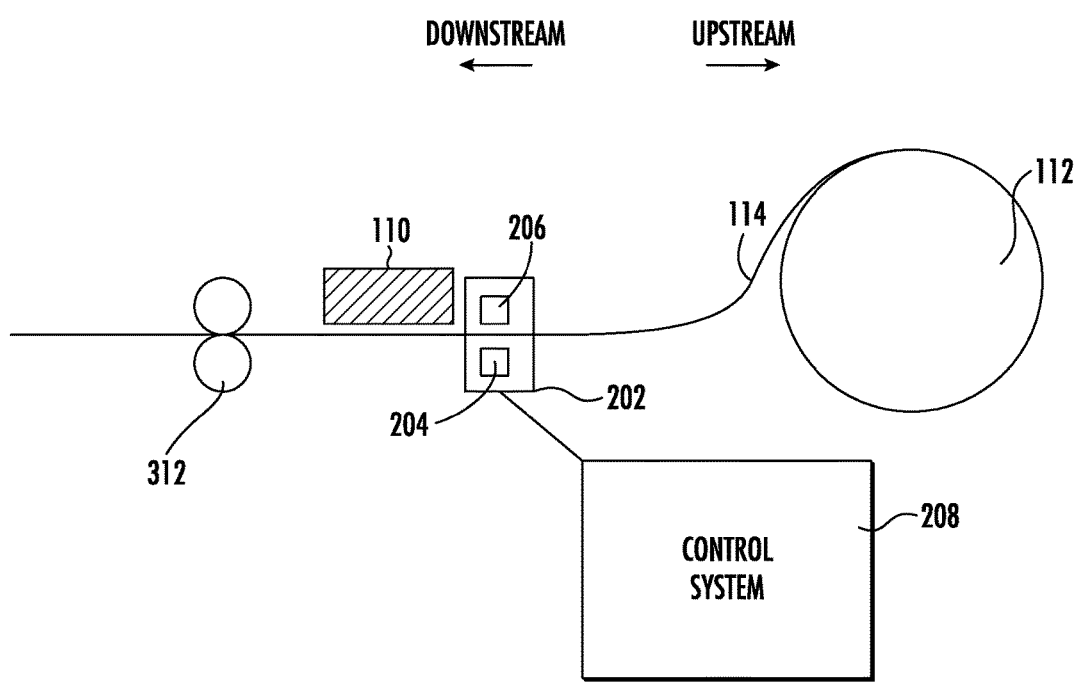

FIGS. 1A, 1B, and 1C depict the printer 100 as the thermal transfer printer. However, in some embodiments, the scope of the disclosure is not limited to the printer 100 being a thermal transfer printer. In alternate embodiments, the printer 100 may correspond to a direct thermal printer, as is further described in conjunction with FIG. 3A and FIG. 3B. FIGS. 3A and 3B illustrate a perspective view and a schematic of an example direct thermal printer 300, respectively, according to one or more embodiments described herein.

Referring to FIG. 3A, the direct thermal printer 300 includes a housing 302 that includes a top cover 303 and a main body 304. The top cover 303 is pivotally coupled to the main body 304. Further, the top cover 303 receives the print head 110. The main body 304 of the direct thermal printer 300 has a print bed 306 from which a pair of media support members 308 extends in an upward direction. The pair of media support members 308 is configured to receive the media roll 112. In an example embodiment, the media 114 in the media roll 112 corresponds to a thermal print media.

In an example embodiment, the main body 304 is further configured to receive a media drive 312 is configured to cause the media 114 to traverse from the media roll 112 to a printer media output 104. When the direct thermal printer 300 executes a print job, the print head 110 may directly press against the media 114 to print content on the media 114. Since the media 114 is a thermal media, therefore, on application of heat (through the plurality of heating elements on the print head 110 is pressed against the media 114) the content gets printed on the media 114.

Referring to FIG. 3B, the direct thermal printer 300 further includes the media sensor 202 and the control system 208.

For the purpose of ongoing description, the various embodiments of the present disclosure have been described in view of the printer 100. However, the embodiments described herein are also applicable of the direct thermal printer 300, without departing from the scope of the disclosure.

Figure 4:
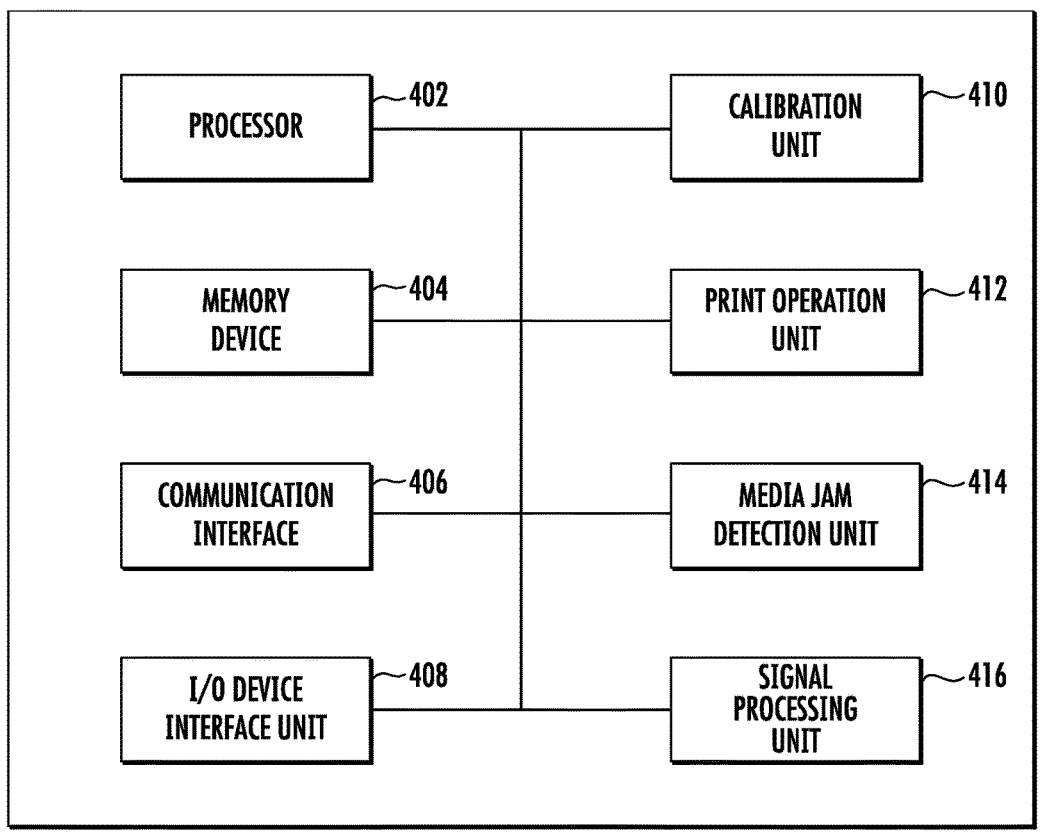
FIG. 4. illustrates a block diagram of a control system, according to one or more embodiments described herein.

FIG. 4. illustrates a block diagram of the control system 208, according to one or more embodiments described herein. The control system 208 includes a processor 402, a memory device 404, a communication interface 406, an input/output (I/O) device interface unit 408, a calibration unit 410, a print operation unit 412, a media jam detection unit 414, and a signal processing unit 416. In an example embodiment, the processor 402 may be communicatively coupled to each of the memory device 404, the communication interface 406, the I/O device interface unit 408, the calibration unit 410, the print operation unit 412, the media jam detection unit 414, and the signal processing unit 416.

The processor 402 may be embodied as a means including one or more microprocessors with accompanying digital signal processor(s), one or more processor(s) without an accompanying digital signal processor, one or more coprocessors, one or more multi-core processors, one or more controllers, processing circuitry, one or more computers, various other processing elements including integrated circuits such as, for example, an application specific integrated circuit (ASIC) or field programmable gate array (FPGA), or some combination thereof. Accordingly, although illustrated in FIG. 4 as a single processor, in an embodiment, the processor 402 may include a plurality of processors and signal processing modules. The plurality of processors may be embodied on a single electronic device or may be distributed across a plurality of electronic devices collectively configured to function as the circuitry of the control system 208. The plurality of processors may be in operative communication with each other and may be collectively configured to perform one or more functionalities of the circuitry of the control system 208, as described herein. In an example embodiment, the processor 402 may be configured to execute instructions stored in the memory device 404 or otherwise accessible to the processor 402. These instructions, when executed by the processor 402, may cause the circuitry of the control system 208 to perform one or more of the functionalities, as described herein.

Whether configured by hardware, firmware/software methods, or by a combination thereof, the processor 402 may include an entity capable of performing operations according to embodiments of the present disclosure while configured accordingly. Thus, for example, when the processor 402 is embodied as an ASIC, FPGA or the like, the processor 402 may include specifically configured hardware for conducting one or more operations described herein. Alternatively, as another example, when the processor 402 is embodied as an executor of instructions, such as may be stored in the memory device 404, the instructions may specifically configure the processor 402 to perform one or more algorithms and operations described herein.

Thus, the processor 402 used herein may refer to a programmable microprocessor, microcomputer or multiple processor chip or chips that can be configured by software instructions (applications) to perform a variety of functions, including the functions of the various embodiments described above. In some devices, multiple processors may be provided dedicated to wireless communication functions and one processor dedicated to running other applications. Software applications may be stored in the internal memory before they are accessed and loaded into the processors. The processors may include internal memory sufficient to store the application software instructions. In many devices, the internal memory may be a volatile or nonvolatile memory, such as flash memory, or a mixture of both. The memory can also be located internal to another computing resource (e.g., enabling computer readable instructions to be downloaded over the Internet or another wired or wireless connection).

The memory device 404 may include suitable logic, circuitry, and/or interfaces that are adapted to store a set of instructions that is executable by the processor 402 to perform predetermined operations. Some of the commonly known memory implementations include, but are not limited to, a hard disk, random access memory, cache memory, read only memory (ROM), erasable programmable read-only memory (EPROM) & electrically erasable programmable read-only memory (EEPROM), flash memory, magnetic cassettes, magnetic tape, magnetic disk storage or other magnetic storage devices, a compact disc read only memory (CD-ROM), digital versatile disc read only memory (DVD-ROM), an optical disc, circuitry configured to store information, or some combination thereof. In an embodiment, the memory device 404 may be integrated with the processor 402 on a single chip, without departing from the scope of the disclosure.

The communication interface 406 may correspond to a communication interface that may facilitate transmission and reception of messages and data to and from various devices. For example, the communication interface 406 is communicatively coupled with a computing device (not shown). Examples of the communication interface 406 may include, but are not limited to, an antenna, an Ethernet port, a USB port, a serial port, or any other port that can be adapted to receive and transmit data. The communication interface 406 transmits and receives data and/or messages in accordance with the various communication protocols, such as, I2C, TCP/IP, UDP, and 4G, 4G, or 4G communication protocols.

The I/O device interface unit 408 may include suitable logic and/or circuitry that may be configured to communicate with the one or more components of the printer 100, in accordance with one or more device communication protocols such as, but not limited to, I2C communication protocol, Serial Peripheral Interface (SPI) communication protocol, Serial communication protocol, Control Area Network (CAN) communication protocol, and 1-Wire® communication protocol. In an example embodiment, the I/O device interface unit 408 may communicate with the media sensor 202 and the electrical drives associated with the media hub 102, the ribbon drive assembly 106, and the ribbon take-up hub 108. For example, the I/O device interface unit 408 may receive the input signal from the media sensor 202. Further, for example, the I/O device interface unit 408 may actuate the first electrical drive associated with the media hub 102 to cause the media 114 to traverse along the media path 116. Some examples of the I/O device interface unit 408 may include, but not limited to, a Data Acquisition (DAQ) card, an electrical drives driver circuit, and/or the like.

Figure 6:
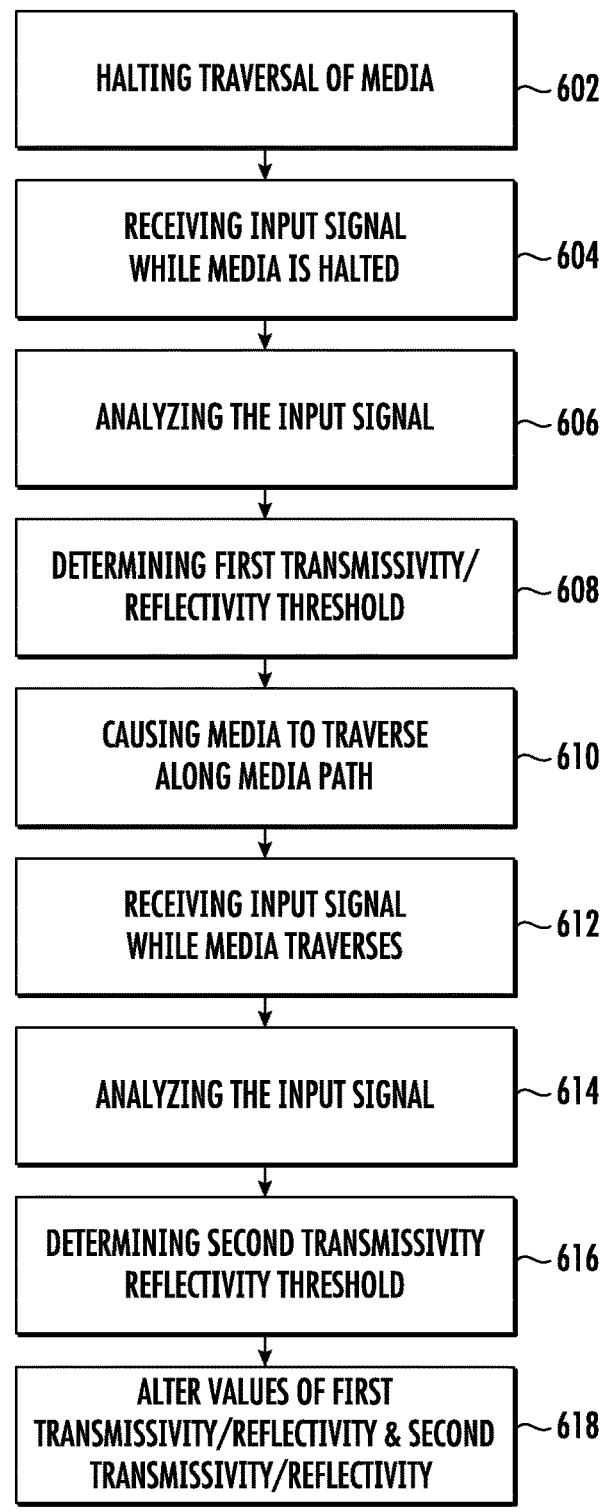
FIG. 6 illustrates a flowchart depicting a method for operating the printer in a calibration mode, according to one or more embodiments described herein.

The calibration unit 410 may include suitable logic and/or circuitry for calibrating the printer 100, as is further described in conjunction with FIG. 6. In an example embodiment, the calibration unit 410 may be configured to determine one or more parameters of the media 114. In an example embodiment, the one or more parameters of the media 114 may include, but may not limited to, a width of the media 114, a type of media 114, and a length of a portion of the media 114. Further, the calibration unit 410 may be configured cause the signal processing unit 416 to determine one or more characteristics of the input signal, received from the media sensor 202 during the calibration of the printer 100, as is further described in conjunction with FIG. 7. In an example embodiment, the one or more characteristics of the input signal may include a measure of an amplitude of the input signal and/or a measure of a frequency of the input signal. Further, based on the one or more characteristics of the input signal, the calibration unit 410 may be further configured to determine a first transmissivity/reflectivity threshold value and a second transmissivity/reflectivity threshold value, as is further described in FIG. 6. Further, the calibration unit 410 may be configured to store the one or more characteristics of the input signal, the first transmissivity/reflectivity threshold value and the second transmissivity/reflectivity threshold value in the memory device 404. The calibration unit 410 may be implemented using one or more technologies, such as, but not limited to, FPGA, ASIC, and the like.

Figure 11:
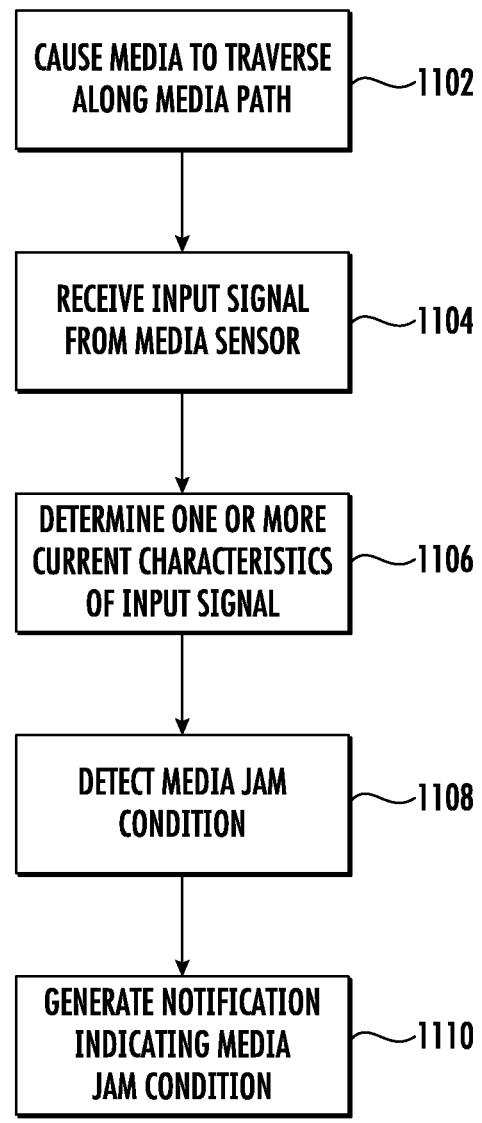
FIG. 11 illustrates a flowchart for operating the printer in a printing mode, according to one or more embodiments described herein.

The print operation unit 412 may include suitable logic and/or circuitry that may cause the printer 100 to perform a print operation, as is further described in conjunction with FIG. 11. In an example embodiment, the print operation unit 412 may be configured to receive a print job from the computing device. Thereafter, the print operation unit 412 may be configured to perform the print operation based on the print job. For instance, during the print operation, the print operation unit 412 may be configured to instruct the I/O device interface unit 408 to actuate the electrical drives associated with the media hub 102, the ribbon drive assembly 106, and ribbon take-up hub 108, to cause the traversal of the media 114 and the ribbon 120 along the media path 116 and the ribbon path 122, respectively. Further, the print operation unit 412 may be configured to control the operation of the print head 110 (for example energization of the one or more heating elements and the vertical translation of the print head 110) to perform the print operation. The print operation unit 412 may be implemented using one or more technologies, such as, but not limited to, FPGA, ASIC, and the like.

The media jam detection unit 414 may include suitable logic and/or circuitry for detecting a media jam condition. In an example embodiment, the media jam condition may correspond to a condition in which the media 114 fails to traverse along the media path 116. In an example embodiment, the media jam detection unit 414 may be configured to detect the media jam condition based on the one or more characteristics of the input signal, as is further described in conjunction with FIG. 12. The media jam detection unit 414 may be implemented using one or more technologies, such as, but not limited to, FPGA, ASIC, and/or the like.

The signal processing unit 416 may include suitable logic and/or circuitry for analyzing the input signal received from the media sensor 202. In an example embodiment, the signal processing unit 416 may include a digital signal processor that may be configured to analyze the input signal to determine the one or more characteristics of the input signal. Further, the signal processing unit 416 may utilize one or more signal processing techniques such as, but not limited to, Fast Fourier Transform (FFT), Discrete Fourier Transform (DFT), Discrete Time Fourier Transform (DTFT) to analyze the input signal. The media jam detection unit 414 may be implemented using one or more technologies, such as, but not limited to, FPGA, ASIC, and the like.

FIGS. 5-7 and 9-12 illustrate example flowcharts of the operations performed by an apparatus, such as the printer 100 of FIGS. 1A, 1B, and 1C in accordance with example embodiments of the present invention. It will be understood that each block of the flowcharts, and combinations of blocks in the flowcharts, may be implemented by various means, such as hardware, firmware, one or more processors, circuitry and/or other devices associated with execution of software including one or more computer program instructions. For example, one or more of the procedures described above may be embodied by computer program instructions. In this regard, the computer program instructions which embody the procedures described above may be stored by a memory of an apparatus employing an embodiment of the present invention and executed by a processor in the apparatus. As will be appreciated, any such computer program instructions may be loaded onto a computer or other programmable apparatus (e.g., hardware) to produce a machine, such that the resulting computer or other programmable apparatus provides for implementation of the functions specified in the flowcharts' block(s). These computer program instructions may also be stored in a non-transitory computer-readable storage memory that may direct a computer or other programmable apparatus to function in a particular manner, such that the instructions stored in the computer-readable storage memory produce an article of manufacture, the execution of which implements the function specified in the flowcharts' block(s). The computer program instructions may also be loaded onto a computer or other programmable apparatus to cause a series of operations to be performed on the computer or other programmable apparatus to produce a computer-implemented process such that the instructions which execute on the computer or other programmable apparatus provide operations for implementing the functions specified in the flowcharts' block(s). As such, the operations of FIGS. 5-7 and 9-12, when executed, convert a computer or processing circuitry into a particular machine configured to perform an example embodiment of the present invention. Accordingly, the operations of FIGS. 5-7 and 9-12 define an algorithm for configuring a computer or processor, to perform an example embodiment. In some cases, a general purpose computer may be provided with an instance of the processor which performs the algorithm of FIGS. 5-7 and 9-12 to transform the general purpose computer into a particular machine configured to perform an example embodiment.

Accordingly, blocks of the flowchart support combinations of means for performing the specified functions and combinations of operations for performing the specified functions. It will also be understood that one or more blocks of the flowcharts', and combinations of blocks in the flowchart, can be implemented by special purpose hardware-based computer systems which perform the specified functions, or combinations of special purpose hardware and computer instructions.

Figure 5:
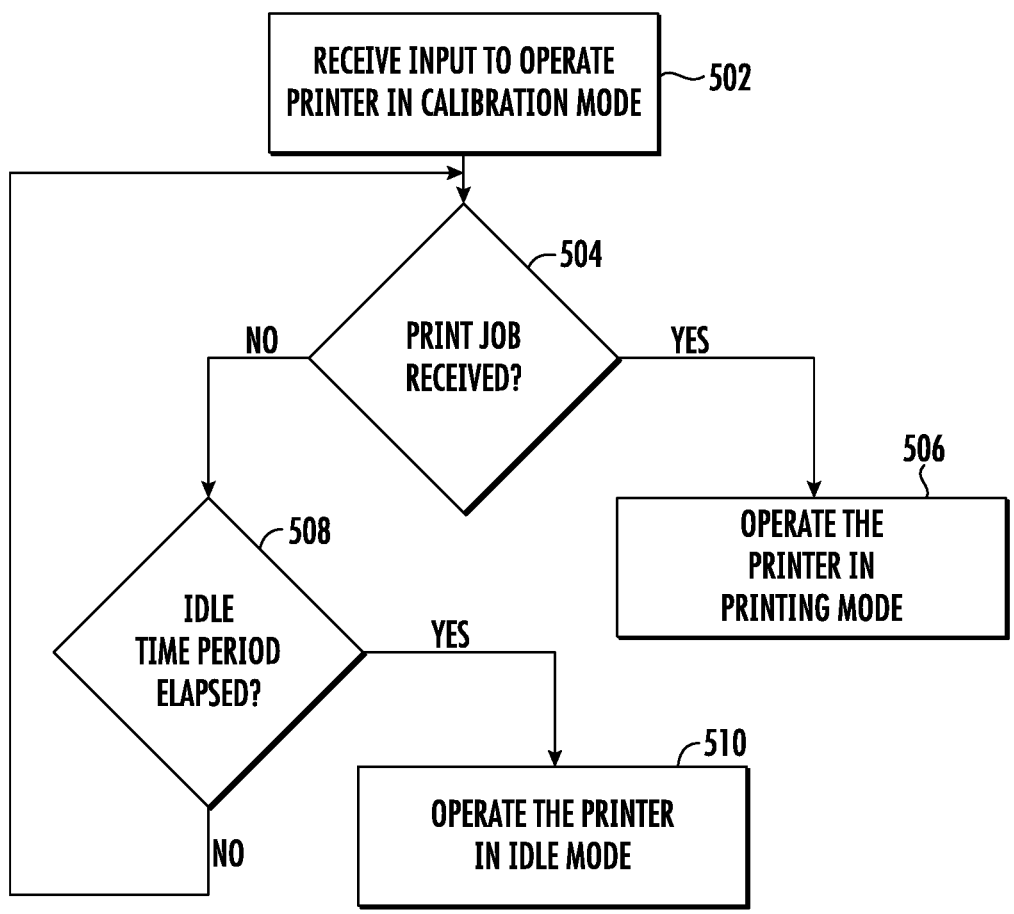
FIG. 5 illustrates a flowchart depicting a method for operating the printer, according to one or more embodiments described herein.

FIG. 5 illustrates a flowchart 500 depicting a method for operating the printer 100, according to one or more embodiments described herein.

At step 502, the printer 100 includes means such as, the control system 208, the processor 402, the calibration unit 410, and/or the like, for receiving an input from the user of the printer 100 to operate the printer in the calibration mode, which is further described with respect to FIG. 6. In some embodiments, the user of the printer 100 provides the input (corresponding to operating the printer 100 in the calibration mode) by pressing a button (not shown) provided on the printer 100 in a predetermined pattern. In an example embodiment, the predetermined pattern may correspond to pressing the button in a predetermined sequence or for a predetermined time duration. For example, if the user keeps the button pressed for 10 seconds, the processor 402 may determine that the printer 100 is to be operated in the calibration mode. In an example embodiment, the predetermined pattern is pre-configured during manufacturing of the printer 100.

FIG. 6 illustrates a flowchart 600 depicting a method for operating the printer 100 in the calibration mode, according to one or more embodiments described herein. The flowchart 600 has been described in conjunction with the FIGS. 1A, 1B, 1C, and 2-5.

At step 602, the printer 100 includes means such as, the control system 208, the processor 402, the calibration unit 410, the I/O device interface unit 408, and/or the like, for halting a traversal of the media 114 along the media path 116. In an example embodiment, the processor 402 may be configured to instruct the I/O device interface unit 408 to halt the actuation of the first electrical drive, the second electrical drive, and the third electrical drive. As discussed above, the first electrical drive, the second electrical drive, and the third electrical drive are associated with the media hub 102, the ribbon drive assembly 106, and the ribbon take-up hub 108, respectively. Therefore, halting the actuation of the first electrical drive, the second electrical drive, and the third electrical drive, halts the traversal of the media 114 and the ribbon 120. Since the media 114 traversal halts, the media 114 is stationary with respect to the print head 110 and the media sensor 202.

At step 604, the printer 100 includes means such as, the control system 208, the processor 402, the calibration unit 410, the I/O device interface unit 408, and/or the like, for receiving the input signal from the media sensor 202, while the media 114 is stationary with respect to the print head 110. As discussed supra, the input signal corresponds to the voltage signal that is representative of the transmissivity/reflectivity of the media 114. Further, as discussed supra, the transmissivity/reflectivity of the media 114 is determined based on the intensity of the portion of the light signal reflected from or transmitted through the media 114. Therefore, the input signal generated by the media sensor 202 is representative of the intensity of the portion of the light signal received by the media sensor 202. More specifically, the one or more characteristics of the input signal (such as the amplitude and frequency) of the input signal are representative of the intensity of the portion of the light signal received by the media sensor 202. For example, if the intensity of the portion of light signal received at a first time instant is greater than the intensity of the portion of the light signal received at a second time instant, the amplitude of the input signal received at the first time instant is greater than the intensity of the input signal received at the second time instant. An example input signal received while the media is stationary during operation of the printer 100 in the calibration mode is illustrated in conjunction with FIG. 8.

At step 606 the printer 100 includes means such as, the control system 208, the processor 402, the calibration unit 410, the signal processing unit 416, and/or the like, for analyzing the input signal received from the media sensor 202 while the traversal of the media 114 is halted. In an example embodiment, the calibration unit 410 may instruct the signal processing unit 416 to analyze the input signal. The analysis of the input signal has been further described in conjunction with FIG. 7.

Figure 7:
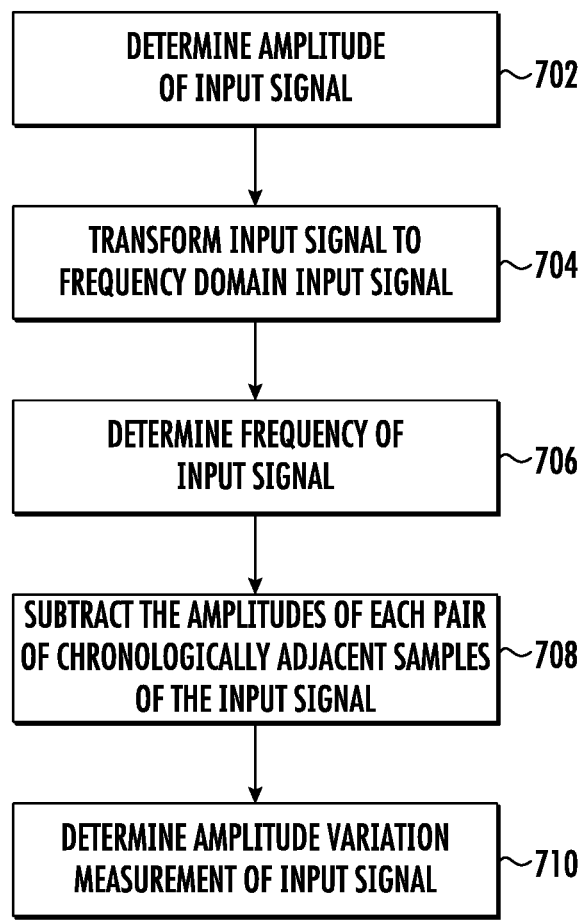
FIG. 7 illustrates a flowchart depicting a method for analyzing an input signal, according to the one or more embodiments described herein.

FIG. 7 illustrates a flowchart 700 depicting a method for analyzing the input signal, according to the one or more embodiments described herein.

At step 702, the printer 100 includes means such as, the control system 208, the processor 402, the signal processing unit 416, and/or the like, for determining the amplitude of the input signal. In some examples, based on extrinsic/intrinsic factors such as thermal variations, shot noise phenomena, and/or the like, the input signal generated by the media sensor 202, while the media 114 is stationary, may be noisy. To this end, the amplitude and the frequency of the input signal may not be constant. As such, the signal processing unit 416 may be configured to determine an average of the amplitude of the input signal (received while the media 114 is halted). As discussed above, the media sensor 202 may be configured to generate the input signal in accordance with the sampling rate associated with the media sensor 202. Therefore, to determine the average amplitude of the input signal, the signal processing unit 416 may be configured to receive the input signal from the media sensor 202 for a predefined time duration within which the signal processing unit 416 may receive samples (determined based on the sampling rate associated with the media sensor 202) of the input signal. Thereafter, the signal processing unit 416 may be configured to determine the average amplitude of the input signal by determining the average of the amplitudes of the received samples of the input signal. In some examples, the signal processing unit 416 may determine the amplitude of the input signal as the average of the amplitude of the input signal.

In another embodiment, the signal processing unit 416 may be configured to determine a maximum amplitude of the input signal, while the media 114 is stationary with respect to the media sensor 202, as the amplitude of the input signal. For example, the signal processing unit 416 may be configured to identify a sample of the input signal having maximum amplitude among the amplitudes of the received samples of the input signal. Thereafter, the signal processing unit 416 may be configured to determine the amplitude of the identified sample as the amplitude of the input signal.

Alternatively or additionally, the signal processing unit 416 may be configured to determine a variance in the amplitude of the input signal (received while the media 114 is halted). In an example embodiment, the signal processing unit 416 may be configured to determine variances in the amplitude of the input signal based on the average amplitude of the input signal and the measure of the amplitude at various time instants. For example, the signal processing unit 216 may determine the average amplitude of the input signal as 1 volt. Further, the signal processing unit 216 determines that the amplitude of the input signal at time instant t1 is 1.1 volts, and at time instant t2 is 1.2 volts. Accordingly, the signal processing unit 216 determines the variance as 0.1 volts and 0.2 volts.

Thereafter, the signal processing unit 416 may be configured to determine a maximum variance in amplitude of the input signal among the determined variances of the amplitude of the input signal. For instance, the signal processing unit 416 may determine that 0.2 volts is the maximum variance in the amplitude of the input signal. Thereafter, the signal processing unit 416 may be configured to determine the amplitude associated with the maximum variance as the amplitude of the input signal.

At step 704, the printer 100 includes means such as, the control system 208, the processor 402, the signal processing unit 416, and/or the like, for transforming the input signal in a frequency domain input signal. In an example embodiment, the signal processing unit 416 may be configured to utilize one or more signal processing techniques such as, but not limited to, DFT, DTFT, and/or the like for transforming the input signal in the frequency domain input signal. In some examples, the input signal in the frequency domain (i.e., the frequency domain input signal) is representative of various frequencies present in the input signal. For instance, the frequency domain input signal may have frequencies varying between a range from 10 KHz to 20 KHz. Additionally, the frequency domain input signal includes information pertaining to the amplitude of the input signal at the various frequencies.

At step 706, the printer 100 includes means such as, the control system 208, the processor 402, the signal processing unit 416, and/or the like, for determining the frequency of the input signal. In an example embodiment, the signal processing unit 416 may be configured to determine the various frequencies present in the input signal based on the analysis of the frequency domain input signal. As discussed above, the frequency domain input signal is representative of the various frequencies present in the input signal, therefore, the signal processing unit 416 is able to determine the various frequencies present in the input signal from the frequency domain input signal.

Thereafter, the signal processing unit 416 may be configured to determine the frequency of the input signal as the average of the various frequencies present in the input signal. Alternatively or additionally, the signal processing unit 416 may be configured to determine a maxima of the various frequencies present in the input signal. Thereafter, the signal processing unit 416 may be configured to determine the maximum frequency as the frequency of the input signal. In yet another embodiment, the signal processing unit 416 may be configured to determine the frequency of input signal based on the variance in the various frequencies, as is described above in conjunction with determining the amplitude of the input signal in step 702.

Alternatively or additionally, the signal processing unit 416 may determine the amplitude of the input signal based on the analysis of the frequency domain input signal. As discussed supra, the frequency domain input signal includes information pertaining to the amplitude of the input signal at the various frequencies. Therefore, in some examples, the signal processing unit 416 may be configured to determine the amplitude of the input signal from the frequency domain input signal. To determine the amplitude of the input signal, the signal processing unit 416 may be configured to determine the maximum amplitude of the input signal among the amplitude of the input signal at the various frequencies. Thereafter, in some examples, the signal processing unit 416 may be configured to determine the maximum amplitude as the amplitude of the input signal. In alternate embodiment, the signal processing unit 416 may be configured to determine an average of the amplitude at the various frequencies of the input signal. In some examples, the signal processing unit 416 may be configured to determine the average amplitude as the amplitude of the input signal.

In an example embodiment, the determined amplitude and the determined frequency of the input signal corresponds to the one or more characteristics of the input signal. In some examples, the scope of the disclosure is not limited to the determined amplitude and the determined frequency of the input signal as the one or more characteristics of the input signal. In an example embodiment, the one or more characteristics of the input signal may further include a measure of variation in the amplitude (hereinafter referred as an amplitude variation measurement) of the input signal. To determine the amplitude variation measurement, at step 708, the printer 100 includes means such as, the control system 208, the processor 402, the signal processing unit 416, and/or the like, for subtracting the amplitudes of each pair of chronologically adjacent samples of the input signal to determine a plurality of amplitude variation measurements. Thereafter, at step 710, the printer 100 includes means such as, the control system 208, the processor 402, the signal processing unit 416, and/or the like, for determining amplitude variation measurement of the input signal. In an example embodiment, the signal processing unit 416 may be configured to determine the amplitude variation measurement of the input signal as an average of the plurality of amplitude variation measurements. In an alternative embodiment, the signal processing unit 416 may be configured to determine an average of the variance in the amplitude of the input signal (determined in the step 702) as the amplitude variation measurement.

Referring back to FIG. 6, at step 608, the printer 100 includes means such as, the control system 208, the processor 402, the calibration unit 410, and/or the like, for determining a first transmissivity/reflectivity threshold based on the one or more characteristics of the input signal. In an example embodiment, the calibration unit 410 may determine the first transmissivity/reflectivity threshold as the determined amplitude (determined in the step 702) of the input signal, received while the media 114 is stationary with respect to the media sensor 202. In another embodiment, the calibration unit 410 may determine the first transmissivity/reflectivity threshold as the determined frequency (determined in the step 706) of the input signal, received while the media 114 is stationary with respect to the media sensor 202. In yet another embodiment, the calibration unit 410 may determine the first transmissivity/reflectivity threshold as a combination of the determined amplitude and the determined frequency of the input signal, received while the media 114 is stationary. In yet another embodiment, the calibration unit 410 may determine the first transmissivity/reflectivity threshold as the amplitude variation measurement (determined in the step 710). Hereinafter, the determined amplitude, the determined frequency, and the determined amplitude variation measurement, constituting the first transmissivity/reflectivity threshold have been referred to as a first amplitude threshold, a first frequency threshold, and a first amplitude variation measurement threshold.

At step 610, the printer 100 includes means such as, the control system 208, the processor 402, the calibration unit 410, the I/O device interface unit 408, and/or the like, for causing the media 114 to traverse along the media path 116. In an example embodiment, the calibration unit 410 may be configured to instruct the I/O device interface unit 408 to actuate the first electrical drive associated with the media hub 102. The actuation of the first electrical drive causes the media hub 102 to rotate, which in turn causes the media roll 112 to supply the media 114 along the media path 116. Since the media traverses along the media path 116, therefore, the media path 116 also traverses with respect to the print head 110 and the media sensor 202.

At step 612, the printer 100 includes means such as, the control system 208, the processor 402, the calibration unit 410, the I/O device interface unit 408, and/or the like, for receiving the input signal from the media sensor 202, while the media 114 traverses along the media path 116. In an example embodiment, the since media 114 is not stationary with respect to the media sensor 202 and different portions of the media 114 passes over the media sensor 202, therefore, the measure of the transmissivity/reflectivity varies as the media traverses along the media path 116. Further, in scenarios where the media 114 has the one or more portions that are either separated by means of perforations or by means of marks, the measure transmissivity/reflectivity may observe a sudden spike or sudden fall, as the perforations or marks passes over the media sensor 202. One such example of the input signal received from the media sensor 202, while the media 114 traverses along the media path, has been further described in conjunction with FIG. 8.

At step 614, the printer 100 includes means such as, the control system 208, the processor 402, the calibration unit 410, the signal processing unit 416, and/or the like, for analyzing the input signal received in the step 614 (i.e., while the media 114 traverses along the media path 116). In an example embodiment, the signal processing unit 416 may employ similar methodologies to analyze the input signal, as is described in conjunction with flowchart 700. For example, the signal processing unit 416 may be configured to determine the amplitude of the input signal received in the step 612. As discussed, in some embodiments, the signal processing unit 416 may be configured to determine the maximum amplitude of the input signal (received while the media traverses along the media path), as the amplitude of the input signal. In alternate embodiment, the signal processing unit 416 may be configured to determine the average amplitude of the input signal received while the media traverses along the media path. Thereafter, the signal processing unit 416 may be configured to determine the average amplitude as the amplitude of the input signal.

In addition to determining the amplitude of the input signal (received in the step 612), the signal processing unit 416 may be further configured to determine the frequency of the input signal. As discussed, to determine the frequency, the signal processing unit 416 may be configured to transform the input signal into frequency domain input signal. Thereafter, the signal processing unit 416 may be configured to determine a maximum frequency of the input signal (received while the media traverses along the media path) from the frequency domain input signal. In some embodiments, the signal processing unit 416 may be configured to determine the maximum frequency of the input signal as the frequency of the input signal. In alternate embodiment, the signal processing unit 416 may be configured to determine the average frequency of the input signal from the frequency domain input signal. In some embodiments, the signal processing unit 416 may be configured to determine the average frequency as the frequency of the input signal.

Additionally, the signal processing unit 416 may be configured to determine the amplitude variation measurement of the input signal, received while the media is traversing along the media path, as is described above in the step 708. For example, to determine the amplitude variation measurement, the signal processing unit 416 may be configured to subtract the amplitude of each pair of chronologically adjacent samples of the received samples of the input signal to determine the plurality of amplitude variation measurements. Thereafter, the signal processing unit 416 may be configured to determine the average of the plurality of amplitude variation measurements, and is further configured to determine the average of the plurality of amplitude variation measurements as the amplitude variation measurement of the input signal.

In an example embodiment, the determined frequency of the input signal, the determined amplitude of the input signal, and the determined amplitude variation measurement correspond to the one or more characteristics of the input signal (received while the media traverses along the media path).

At step 616, the printer 100 includes means such as, the control system 208, the processor 402, the calibration unit 410, and/or the like, for determining the second transmissivity/reflectivity threshold based on the one or more characteristics of the input signal received while the media 114 traverses along the media path 116. In some embodiments, the calibration unit 410 may be configured to determine the second transmissivity/reflectivity threshold as the determined amplitude (determined in the step 614) of the input signal, received while the media 114 traverses with respect to the media sensor 202. In another embodiment, the calibration unit 410 may determine the second transmissivity/reflectivity threshold as the determined frequency of the input signal, received while the media 114 traverses with respect to the media sensor 202. In yet another embodiment, the calibration unit 410 may determine the second transmissivity/reflectivity threshold as combination of the determined amplitude and the determined frequency of the input signal, received while the media 114 traverses with respect to the media sensor 202. In yet another embodiment, the calibration unit 410 may determine the second transmissivity/reflectivity threshold as the determined amplitude variation measurement, determined while the media traverses along the media path 116. Hereinafter, the determined amplitude, the determined frequency, and the determined amplitude variation measurement, constituting the second transmissivity/reflectivity threshold have been referred to as a second amplitude threshold, a second frequency threshold, and a second amplitude variation measurement threshold.

As discussed above, when the media 114 traverses along the media path 116, the amplitude of the input signal varies, as various portions of the media 114 passes over the media sensor 202. Therefore, as discussed above, the amplitude of the input signal received while the media 114 traverses along the media path 116 is greater than the amplitude of the input signal received while the media 114 is stationary. Similarly, the frequency of the input signal received while the media 114 traverses along the media path 116 is less than the frequency of the input signal while the media 114 is stationary with respect to the media sensor 202. Accordingly, the determined first frequency threshold is greater than the second frequency threshold. Further, the determined first amplitude threshold is less than the determined second amplitude threshold. Furthermore, when the media 114 traverses along the media path 116, the variation in the amplitude of the input signal is greater than the amplitude of the input signal, received while the media 114 is stationary. Therefore, the first amplitude variation measurement threshold is greater than the amplitude variation measurement threshold. The inputs signal received while the media 114 is stationary and while the media traverses along the media path 116 is further depicted in FIG. 8.

In some embodiments, the first transmissivity/reflectivity threshold and the second transmissivity/reflectivity threshold are utilized to determine a media jam condition while the printer 100 operates in a printing mode. For example, the media jam condition is detected, during the operation of the printer 100 in the printing mode, when the input signal (received during the printing mode) has amplitude less than or equal to the first amplitude threshold, and/or the frequency of the input signal is greater than or equal to the first frequency threshold, and/or the amplitude variation measurement of the input signal is less than or equal to the first amplitude variation measurement threshold. The operation of the printer 100 in the printing mode and the detection of the media jam condition are described later in conjunction with FIG. 11. In an example embodiment, a sensitivity to detect the media jam condition is dependent on the values of the first transmissivity/reflectivity threshold and the second transmissivity/reflectivity threshold. In some embodiments, the sensitivity to detect the media jam condition may be altered by altering the values of the first transmissivity/reflectivity threshold and the second transmissivity/reflectivity threshold. At step 618, the printer 100 includes means, such as the control system 208, the processor 402, and/or the like, for altering the values of the first transmissivity/reflectivity threshold and the second transmissivity/reflectivity threshold, as is described later in conjunction with FIG. 10.

Figure 8:
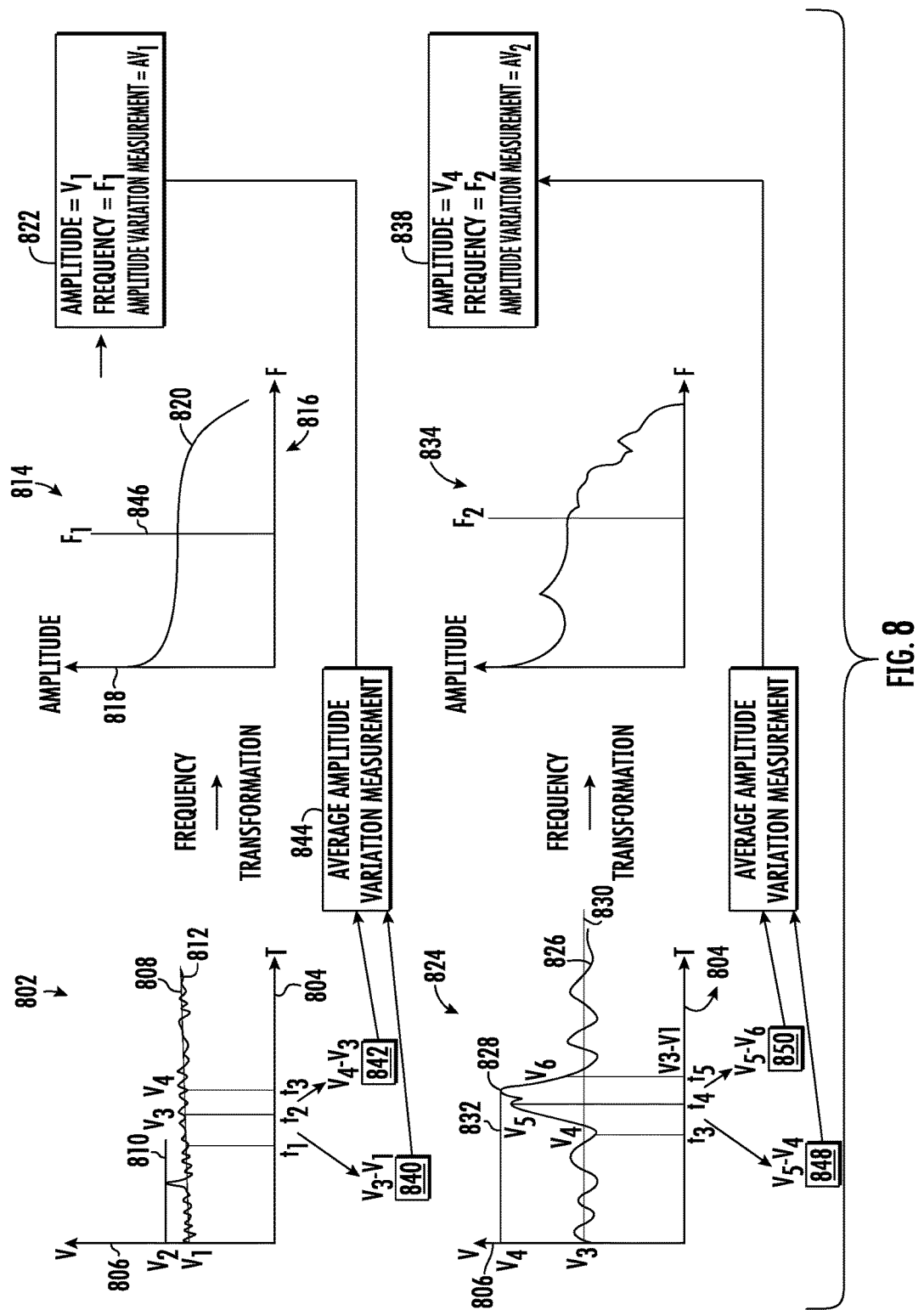
FIG. 8 illustrates an example determination of a first transmissivity/reflectivity threshold and a second transmissivity/reflectivity threshold, from the input signal, according to one or more embodiments described herein.

FIG. 8 illustrates an example determination of the first transmissivity/reflectivity threshold and the second transmissivity/reflectivity threshold, according to one or more embodiments described herein.

As discussed in conjunction with FIG. 6, during calibration mode, the traversal of the media 114 is halted (refer step 604) and thereafter, the input signal is received from the media sensor 202 (refer step 606). Further, as discussed supra, the input signal received while the media 114 is stationary with respect to the media sensor 202 may have a non-constant amplitude and frequency (due to noise), as is illustrated by a graphical representation 802. The graphical representation 802 includes a Y-axis 806 that represents a voltage of the input signal. Further, the graphical representation 802 includes an X-axis 804 representing a time duration, while the media 114 is stationary with respect to the media sensor 202. A curve 808 in the graphical representation 802 corresponds to an example input signal received while the media 114 is stationary with respect to the media sensor 202. Hereinafter, the curve 808 is referred as the example input signal 808. The example input signal 808 depicts non-constant amplitude and frequency. As discussed, the non-constant amplitude and frequency is due to the noise present in the example input signal 808.

The processor 402 may be configured to determine the amplitude of the example input signal 808 (as is described in the step 702). For instance, the processor 402 may be configured to determine the maximum amplitude of the example input signal 808, while the media 114 is stationary.

For example, the maximum amplitude of the example input signal 808 is $V_2$ (e.g., depicted by 810). The processor 402 determines the maximum amplitude, attained by the example input signal 808, as the amplitude of the example input signal 808. In alternate embodiment, the processor 402 determines the average amplitude of the example input signal 808 i.e., $V_1$ (e.g., depicted by 812), as the amplitude of the example input signal 808.

Further, from FIG. 8, it can be observed that the example input signal 808 has an amplitude of $V_1$, V3, and V4, at time instants $t_1$, $t_2$, and $t_3$, respectively. As discussed above, the processor 402 may be configured to determined amplitude variation measurement as $V_3$-$V_1$ (depicted by 840) between time instants $t_2$ and $t_1$. Further, the processor 402 may determine the amplitude variation measurement as $V_4$-$V_3$ (depicted by 842) as the amplitude variation measurement between the time instants $t_2$ and $t_3$. Thereafter, the processor 402 may be configured to determine an average amplitude variation measurement (depicted by 844) based on the amplitude variation measurement 840 (i.e., $V_3$-$V_1$). In some examples, the processor 402 may consider the average amplitude variation measurement 844 as the amplitude variation measurement of the example input signal 808.

Further, as discussed supra, in step 706, the processor 402 may determine the frequency of the example input signal 808 by transforming the example input signal 808 to frequency domain example input signal (e.g., depicted by graphical representation 814). The graphical representation 814 includes the X-axis 816 representing the frequency of the example input signal 808. The graphical representation 814 further includes Y-axis 818 representing the amplitude of the example input signal 808. A curve 820 in the graphical representation 814 represents the frequency domain example input signal. Hereinafter, the curve 820 has been referred as the frequency domain example input signal 820. As described in the step 706, the processor 402 may be configured to determine the average frequency of the example input signal 808 (determined from the frequency domain example input signal 820) as the frequency of the example input signal 808 (e.g., Frequency F1 (depicted by 846)). In alternate embodiment, the processor 402 may be configured to determine the maximum frequency from the frequency domain example input signal 820 as the frequency of the example input signal 808.

Further, the processor 402 may determine the first transmissivity/reflectivity threshold as the combination of the amplitude of the example input signal, the amplitude variation measurement of the input signal, and the frequency of the example input signal (e.g., depicted by 822).

After determining the first transmissivity/reflectivity threshold, the processor 402 may cause the traversal of the media 114 along the media path 116. During the traversal of the media 114, the processor 402 receives the input signal, as is illustrated in graphical representation 824. Similar to the graphical representation 802, the graphical representation 824 includes the Y-axis 806 and X-axis 804 representing the voltage of the input signal and the time, respectively. The curve 826 in the graphical representation 824 represents the input signal received while the media 114 traverses along the media path 116. Hereinafter, the curve 826 is referred to as example input signal 826.

In some embodiments, the example input signal 826 includes peaks 828. The peaks 828 represents sudden increase in the measure of the transmissivity/reflectivity of the media 114, as the media 114 traverses along the media path 116. As discussed supra, the sudden increase in the measure of the transmissivity/reflectivity of the media 114 is indicative of a perforation or a mark passing over the media sensor 202. As discussed, the perforations and the marks are utilized to divide the media 114 into the one or more portions. Therefore, the peaks 828 in the example input signal 826 represents the boundary between two consecutive portions of the media 114.

Further, it can be observed that a variation in the amplitude of the example input signal 826 is much greater than the variation in the amplitude of the example input signal 808. Such variation in the amplitude of the example input signal 826 indicates that the media 114 is traversing along the media path 116. Further, such variations indicate that the measure transmissivity/reflectivity of the media 114 is different at different points.

As discussed above, the processor 402 may be configured to determine the variation in the amplitude of the example input signal 826, as the amplitude variation measurement. In some examples, the processor 402 may be configured to use similar methodologies used to determine the amplitude variation measurement of the example input signal 808. For example, the processor 402 may be configured to determine the amplitude variation measurement as $V_5-V_4$ (depicted by 848) between the time instants $t_3$ and $t_4$. Further, the processor 402 may determine the amplitude variation measurement between the time instants $t_4$ and $t_5$ as $V_5-V_6$ (depicted by 850). Thereafter, the processor 402 may be configured to determine the amplitude variation measurement of the input signal 826 as the average of the amplitude variation measurement 848 and amplitude variation measurement 850.

Further, the processor 402 may determine the average amplitude of the other example input signal 826, as the amplitude of the example input signal 826 (for example the voltage $V_3$ (e.g., depicted by 830)). In alternate embodiment, the processor 402 may determine maximum amplitude of the example input signal 826, as the amplitude of the example input signal 826 (for example the voltage $V_4$ (e.g., depicted by 832)).

Further, the processor 402 may transform the example input signal 826 to generate a frequency domain input signal 834 of the example input signal 826. The processor 402 may determine the frequency of the example input signal 826 from the frequency domain input signal 834. For instance, the processor 402 determines the average frequency $F_2$ (e.g., depicted by 836), as the frequency of the example input signal 826. Further, the processor 402 may consider the determined frequency of the example input signal 826, the determined amplitude variation measurement, and the amplitude of the example input signal 826, as the second transmissivity/reflectivity threshold (e.g., depicted by 838).

In some examples, it can be observed that when the media 114 is stationary, the value of the amplitude of the input signal 808 (received while the media 114 is stationary) is less than the amplitude of the input signal 826 (received when the media 114 is traversing along the media path 116). Further, it can be observed that the value of the frequency of the input signal 808 is greater than the value frequency of the input signal 826 (received while the media 114 traverses along the media path 116). In some examples, as discussed above, the first amplitude threshold and the first frequency threshold correspond to the determined amplitude and determined frequency of the input signal (received while the media 114 is stationary), respectively. Further, the second amplitude threshold and the second frequency threshold correspond to the determined amplitude and determined frequency of the input signal (received while the media 114 traverses along the media path 116), respectively. Therefore, the value of the first frequency threshold is greater than the second frequency threshold. Further, the value of the first amplitude threshold is less than the second amplitude threshold.

In some embodiments, the scope of the disclosure is not limited to the determining the first transmissivity/reflectivity threshold while the printer 100 operates in the calibration mode. Alternatively or additionally, the first transmissivity/reflectivity threshold may be determined while the printer 100 operates in the idle mode, which is further described in conjunction with FIG. 5 and FIG. 9.

Referring back to FIG. 5, at step 504, the printer 100 includes means such as, the control system 208 the processor 402, and/or the like, for determining whether the printer 100 has received a command to perform the print operation. If the processor 402 determines that the command to perform the print operation is received, the processor 402 may be configured to perform step 506.

At step 506, the printer 100 includes means such as, the control system 208, the processor 402, the print operation unit 412, and/or the like, for operating the printer 100 in the printing mode. The operation of the printer 100 in the printing mode has been described in conjunction with FIG. 11.

If at step 504, the processor 402 determines that the command to perform the print operation is not received, the processor 402 may be configured to perform the step 508. At step 508, the printer 100 includes means such as, the control system 208 the processor 402, and/or the like, for determining whether an idle time period has elapsed. In an example embodiment, the idle time period corresponds to a time period within which if the command to perform the print operation is not received, the printer 100 is configured to be operated in the idle mode. If the processor 402, at the step 508, determines that the idle time period has elapsed, the processor 402 may be configured to perform the step 510. However, if the processor 402 determines that the idle time period has not elapsed, the processor 402 may be configured to repeat the step 504.

At step 510, the printer 100 includes means such as, the control system 208 the processor 402, and/or the like, for operating the printer 100 in the idle mode. The operation of the printer 100 in the idle mode has been further described in conjunction with FIG. 9.

Figure 9:
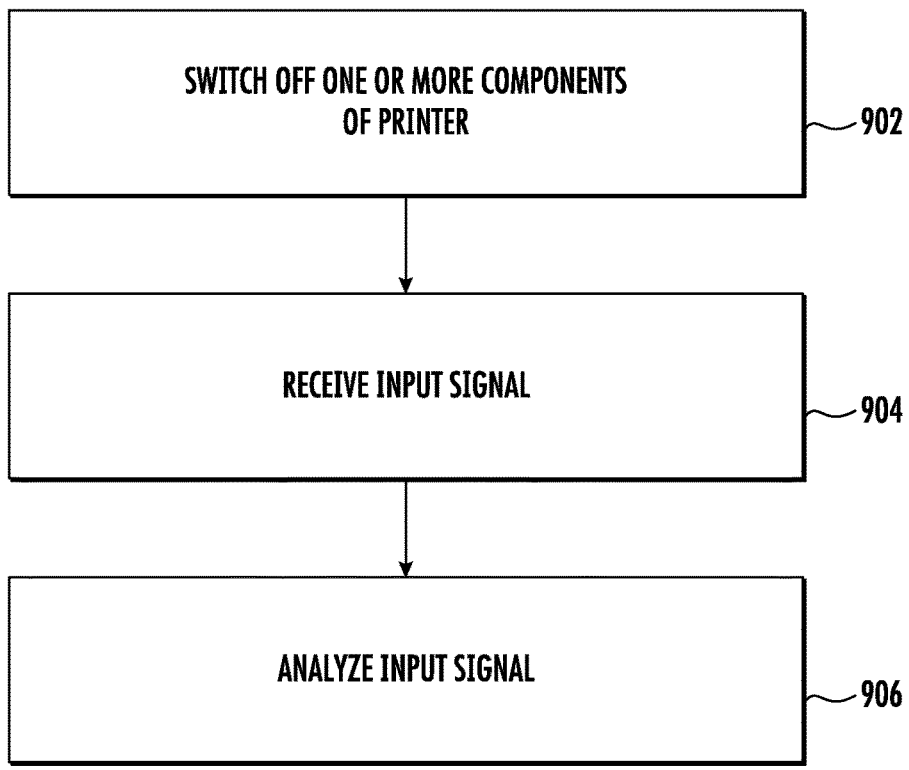
FIG. 9 illustrates a flowchart depicting a method for operating the printer in an idle mode, according to the one or more embodiments described herein.

FIG. 9 illustrates a flowchart 900 depicting a method for operating the printer 100 in the idle mode, according to the one or more embodiments described herein.

At step 902, the printer 100 includes means such as, the control system 208 the processor 402, and/or the like, for switching OFF the one or more components of the printer 100. For example, the processor 402 may be configured to switch OFF the first electrical drive, the second electrical drive, and the third electrical drive. Further, the processor 402 may be configured to switch OFF the print head 110. Switching OFF the one or more components of the printer 100 conserves energy usually consumed by the one or more components.

As the first electrical drive, the second electrical drive, and the third electrical drive are switched OFF, therefore, the media 114 is stationary with respect to the print head 110 and the media sensor 202. As the media 114 is stationary with respect to the media sensor 202, the processor 402 may determine the first transmissivity/reflectivity threshold while the printer 100 operates in the idle mode.

At step 904, the printer 100 includes means such as, the control system 208, the processor 402, the I/O device interface unit 408, and/or the like, for receiving the input signal from the media sensor 202, while the printer 100 operates in the idle mode.

At step 906, the printer 100 includes means such as, the control system 208, the processor 402, the signal processing unit 416, and/or the like, for analyzing the input signal in a similar manner as described in the flowchart 700. For example, the signal processing unit 416 may be configured to determine the amplitude of the input signal. In some embodiments, the signal processing unit 416 may be configured to determine the maximum amplitude of the input signal (received while the printer 100 operates in the idle mode), as the amplitude of the input signal. In alternate embodiment, the signal processing unit 416 may be configured to determine the average amplitude of the input signal (received while the printer 100 operates in the idle mode) as the amplitude of the input signal.

In addition to determining the amplitude of the input signal, the signal processing unit 416 may be further configured to determine the frequency of the input signal. As discussed, to determine the frequency, the signal processing unit 416 may be configured to transform the input signal into frequency domain input signal. Thereafter, the signal processing unit 416 may be configured to determine a maximum frequency of the input signal (received while the printer operates in the idle mode) from the frequency domain input signal. In some embodiments, the signal processing unit 416 may be configured to determine the maximum frequency of the input signal as the frequency of the input signal. In alternate embodiment, the signal processing unit 416 may be configured to determine an average frequency of the input signal from the frequency domain input signal. In some embodiments, the signal processing unit 416 may be configured to determine the average frequency as the frequency of the input signal.

Additionally, as discussed above, the signal processing unit 416 may be configured to determine the amplitude variation measurement of the input signal. For example, the signal processing unit 416 may be configured to determine the amplitude variation measurement between two chronologically adjacent samples of the input signal by subtracting the amplitude of one sample from the other. Thereafter, the signal processing unit 410 may be configured to determine the average of the amplitude variation measurements. Further, the signal processing unit 410 may be configured to consider the average of the amplitude variation measurements as the amplitude variation measurement of the input signal. The determined frequency of the input signal, the determined amplitude variation measurement, and the determined amplitude of the input signal (determined while the printer operates in the idle mode) corresponds to the one or more characteristics of the input signal.

Thereafter, at step 908, the 100 includes means such as, the control system 208, the processor 402, and/or the like, for determining the first transmissivity/reflectivity threshold based on the one or more characteristics of the input signal received while the printer 100 operates in the idle mode. In some embodiments, the processor 402 may be configured to determine the first transmissivity/reflectivity threshold as the determined amplitude (determined in the step 906) of the input signal, received while the printer 100 operates in the idle mode. In another embodiment, the processor 402 may determine the first transmissivity/reflectivity threshold as the determined frequency of the input signal (determined in the step 906). In yet another embodiment, the processor 402 may determine the first transmissivity/reflectivity threshold as combination of the determined amplitude and the determined frequency of the input signal, received while the printer 100 operates in the idle mode. In yet another embodiment, the processor 402 may determine the first transmissivity/reflectivity threshold as the determined amplitude variation measurement of the input signal, received while the printer 100 operates in the idle mode.

Figure 10:
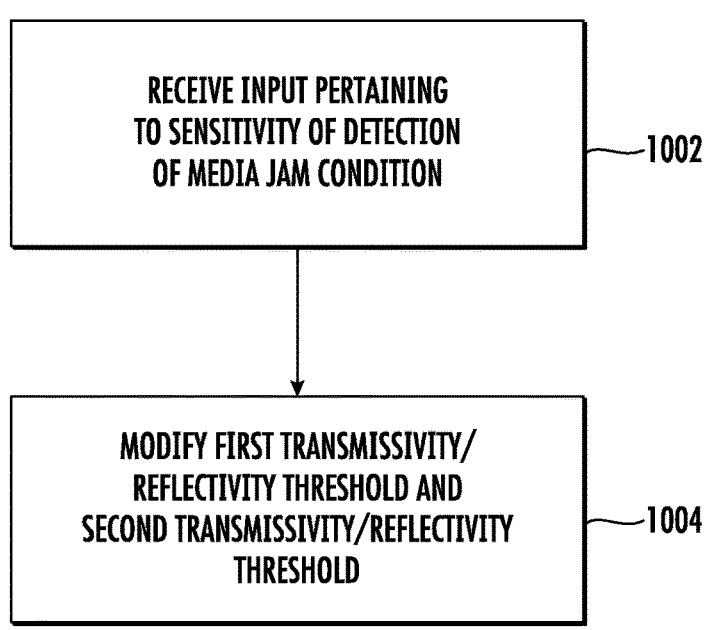
FIG. 10 illustrates a flowchart of a method for modifying the first transmissivity/reflectivity threshold and the second transmissivity/reflectivity threshold, according to one or more embodiments described herein.

FIG. 10 illustrates a flowchart 1000 of a method for modifying the first transmissivity/reflectivity threshold and the second transmissivity/reflectivity threshold, according to one or more embodiments described herein.

At step 1002, the printer 100 includes means such as, the control system 208, the processor 402, and/or the like, for receiving an input pertaining to the sensitivity of detection of the media jam condition. In an example embodiment, the user of the printer 100 may provide the input pertaining to the sensitivity of the media jam condition. For example, the user may provide input through an input panel (not shown) on the printer 100. In some example embodiments, the input may correspond to a percentage value of the sensitivity (hereinafter referred to as sensitivity percentage). For example, the user may provide the input that sensitivity to detect the media jam condition is +50%. In some examples embodiments, the user may provide such input after the first transmissivity/reflectivity threshold and the second transmissivity/reflectivity threshold have been determined (i.e., after the step 616). In alternate embodiment, the user may provide such input before providing the input to activate the calibration mode of operation of the printer 100 (as described in the step 602).

At step 1004, the printer 100 includes means such as, the control system 208, the processor 402, and/or the like, for modifying the first transmissivity/reflectivity threshold and the second transmissivity/reflectivity threshold by the sensitivity percentage. For example, the first transmissivity/reflectivity threshold comprises is 5 Volts amplitude threshold, 0.5 volts amplitude variation measurement threshold, and 10 Hz frequency threshold. Further, if the sensitivity threshold is +50%, the processor 402 modifies the transmissivity/reflectivity threshold and the second transmissivity/reflectivity threshold by 2.5 Volts amplitude, 0.25 amplitude variation measurement, and 5 Hz Frequency. For example, the modified transmissivity/reflectivity threshold is 7.5 Volts amplitude threshold, 0.75 amplitude variation measurement threshold, and 5 Hz frequency threshold.

In some examples, as discussed above, the media jam condition is detected when the frequency of the input signal, received during the operation of the printer 100 in the printing mode, is greater than or equal to the first frequency threshold, and the amplitude of the input signal, received when the printer 100 operates in the printing mode, is less than or equal to the first amplitude threshold. Therefore, to increase the sensitivity of the media jam condition, the value of the first frequency threshold is reduced by the sensitivity percentage while the value of the first amplitude threshold is increased by the sensitivity threshold. Therefore, the value of the modified first frequency threshold is less than the first frequency threshold (as originally determined) and the value of the modified first amplitude threshold is greater than the first amplitude threshold (as originally determined). Similarly, the processor 402 may modify the second transmissivity/reflectivity threshold. In some embodiments, the user of the printer 100 may reduce the sensitivity to detect the media jam condition. In such scenario, the user may provide the input pertaining the sensitivity percentage as a negative sensitivity percentage value. To this end, the modified first amplitude threshold will be less than the first amplitude threshold determined originally. Further, the modified first frequency threshold will be greater than the first frequency threshold determined originally.

FIG. 11 illustrates a flowchart 1100 for operating the printer 100 in the printing mode, according to one or more embodiments described herein.

At step 1102, the printer 100 includes means such as, the control system 208, the processor 402, the print operation unit 412, the I/O device interface unit 408, and/or the like, for causing the media 114 to traverse along the media path 116. As discussed supra, the processor 402 may be configured to perform the printing operation when the command to perform the print operation is received from the computing device (not shown). In an example embodiment, the command may include the print job to be executed by the printer 100.

In some embodiments, to execute the print job, the processor 402 may be configured to cause the traversal of the media 114 along the media path 116 to either provide the media 114 the print head 110 or to push the printed media (the media on which the content has been printed) out from the printer media output 104. In an example embodiment, to cause the media 114 to traverse along the media path 116, the processor 402 may actuate the first electrical drive (associated with the media hub 102) through the I/O device interface unit 408. On actuation, the first electrical drive causes the media hub 102 to rotate, which in turn causes the media roll 112 to supply the media 114 on the media path 116.

At step 1104, the printer 100 includes means such as, the control system 208, the processor 402, the print operation unit 412, the I/O device interface unit 408, and/or the like, for receiving the input signal from the media sensor 202.

At step 1106, the printer 100 includes means such as, the control system 208, the processor 402, the print operation unit 412, the signal processing unit 416, and/or the like, for determining one or more current characteristics of the input signal received in the step 1104. In an example embodiment, the one or more current characteristics of the input signal comprises a current amplitude, a current amplitude variation measurement, and a current frequency of the input signal. In an example embodiment, the current amplitude and current frequency of the input signal may correspond to a measure of the amplitude and frequency of the input signal, received from media sensor 202, in a current time instant. Further, the measure of the current amplitude and current frequency corresponds to actual values of the amplitude and frequency of the input signal in the current time instant. In some examples, the current amplitude variation measurement is indicative of a measure of the variation in the amplitude of the of the input signal between the current time instant and the previous time instant. In an example embodiment, the previous time instant may be determined based on the sampling rate of the media sensor 202.

At step 1108, the printer 100 includes means such as, the control system 208, the processor 402, the print operation unit 412, the media jam detection unit 414, and/or the like, for detecting the media jam condition. The detection of the media jam condition has been further described in conjunction FIG. 12.

Figure 12:
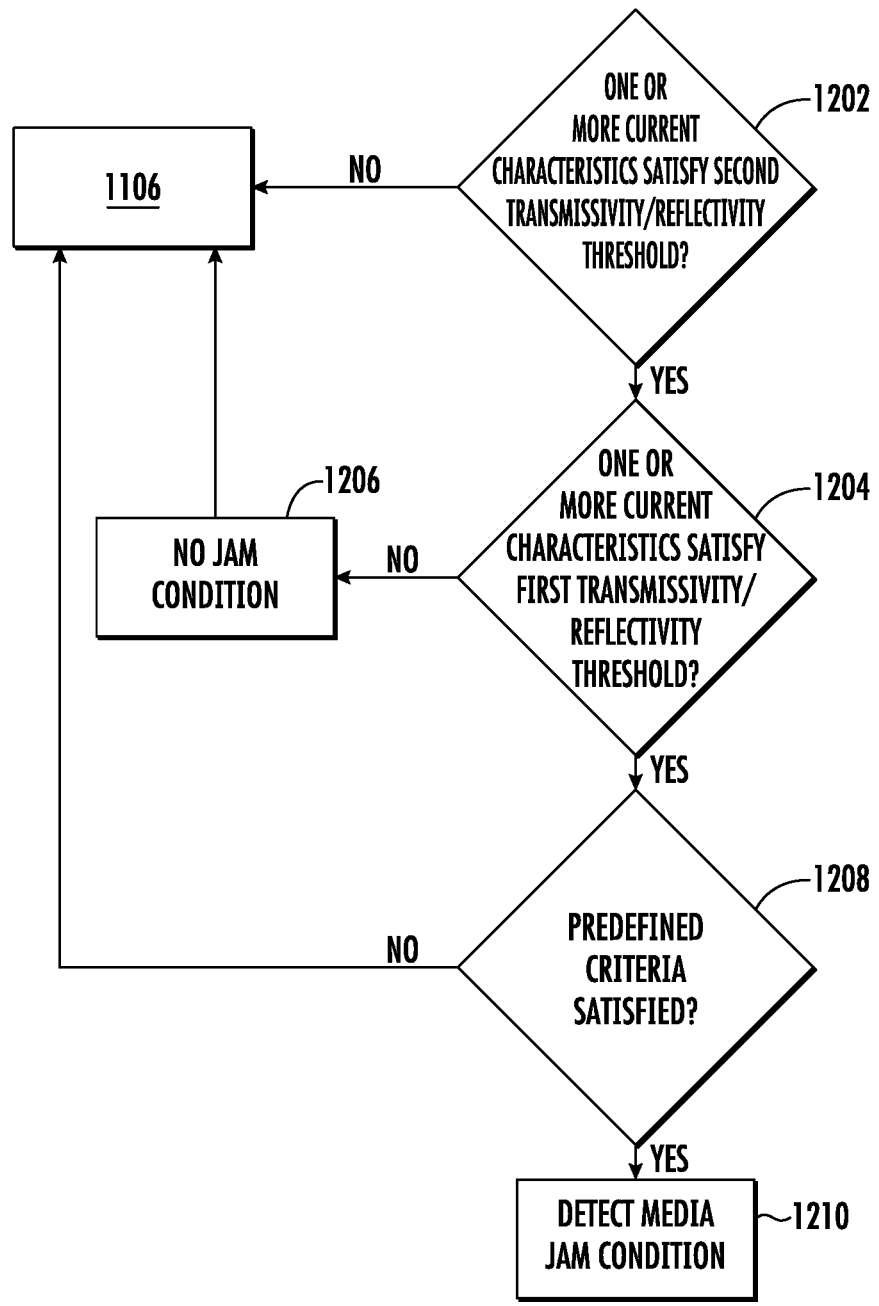
FIG. 12 illustrates a flowchart of a method for detecting a media jam condition, according to one or more embodiments described herein.

FIG. 12 illustrates a flowchart 1200 of a method for detecting the media jam condition, according to one or more embodiments described herein.

At step 1202, the printer 100 includes means such as, the control system 208, the processor 402, the media jam detection unit 414, and/or the like, for determining whether the one or more current characteristics satisfy the second transmissivity/reflectivity threshold. As discussed, the second transmissivity/reflectivity threshold comprises the second amplitude threshold, the second amplitude variation measurement, and the second frequency threshold. Further, as discussed above, the one or more current characteristics of the input signal comprise the current amplitude of the input signal, the current amplitude variation measurement, and the current frequency of the input signal.

In an example embodiment, to determine whether the one or more current characteristics satisfy the second transmissivity/reflectivity threshold, the media jam detection unit 414 may be configured to determine whether the current amplitude of the input signal is less than the second amplitude threshold, while the current frequency of the input signal is greater than the second frequency threshold. Further, the media jam detection unit 414 may be configured to determine whether the current amplitude variation measurement is less than the second amplitude variation measurement threshold.

If the media jam detection unit 414 determines that the current amplitude of the input signal is less than the second amplitude threshold, the current amplitude variation measurement is less than the second amplitude variation measurement threshold, and the current frequency of the input signal is greater than the second frequency threshold, the media jam detection unit 414 may determine that the one or more current characteristics of the input signal satisfy the second transmissivity/reflectivity threshold. In alternate embodiment, if media jam detection unit 414 determines that only the current amplitude of the input signal is less than the second amplitude threshold, the media jam detection unit 414 may determine that the one or more current characteristics of the input signal satisfy the second transmissivity/reflectivity threshold. In yet another embodiment, if media jam detection unit 414 determines that only the current frequency of the input signal is greater than the second frequency threshold, the media jam detection unit 414 may determine that the one or more current characteristics of the input signal satisfy the second transmissivity/reflectivity threshold. In yet another embodiment, if the media jam detection unit 414 determines that only the current amplitude variation measurement is less than the second amplitude variation measurement threshold, the media jam detection unit 414 may determine that the one or more current characteristics of the input signal satisfy the second transmissivity/reflectivity threshold.

If the media jam detection unit 414 determines that the one or more current characteristics of the input signal satisfy the second transmissivity/reflectivity threshold, the media jam detection unit 414 may perform the step 1204. However, if the media jam detection unit 414 determines that the one or more current characteristics of the input signal does not satisfy the second transmissivity/reflectivity threshold, the media jam detection unit 414 may be configured to repeat the step 1106.

At step 1204, the printer 100 includes means such as, the control system 208, the processor 402, the media jam detection unit 414, and/or the like, for determining whether the one or more current characteristics satisfy the first transmissivity/reflectivity threshold. As discussed, the first transmissivity/reflectivity threshold comprises the first amplitude threshold, the first amplitude variation measurement threshold, and the first frequency threshold. Therefore, to determine whether the one or more current characteristics of the input signal, in an example embodiment, the media jam detection unit 414 may be configured to determine whether the current amplitude of the input signal is less than the first amplitude threshold, while the current frequency of the input signal is greater than the first frequency threshold. Additionally or alternatively, to determine whether the one or more current characteristics of the input signal satisfy the first transmissivity/reflectivity threshold, the media jam detection unit 414 may be configured to determine whether the current amplitude variation measurement of the input signal is less than the first amplitude variation measurement threshold.

If the media jam detection unit 414 determines that the current amplitude is less than or equal to the first amplitude threshold, the current amplitude variation measurement is less than or equal to the first amplitude variation measurement threshold, and the current frequency of the input signal is greater than or equal to the first frequency threshold, the media jam detection unit 414 may determine that the one or more current characteristics of the input signal satisfy the first transmissivity/reflectivity threshold. In alternate embodiment, if media jam detection unit 414 determines that only the current amplitude of the input signal is less than or equal to the first amplitude threshold, the media jam detection unit 414 may determine that the one or more current characteristics of the input signal satisfy the first transmissivity/reflectivity threshold. In yet another embodiment, if media jam detection unit 414 determines that only the current frequency of the input signal is greater than or equal to the first frequency threshold, the media jam detection unit 414 may determine that the one or more current characteristics of the input signal satisfy the first transmissivity/reflectivity threshold. In yet another alternative embodiment, if media jam detection unit 414 determines that only the current amplitude variation measurement of the input signal is less than or equal to the first amplitude variation measurement threshold, the media jam detection unit 414 may determine that the one or more current characteristics of the input signal satisfy the first transmissivity/reflectivity threshold.

If the media jam detection unit 414 determines that the one or more current characteristics of the input signal do not satisfy the first transmissivity/reflectivity threshold, the media jam detection unit 414 may be configured to perform the step 1206.

At step 1206, the printer 100 includes means such as, the control system 208, the processor 402, the media jam detection unit 414, and/or the like, for determining a non-jam condition. In an example embodiment, the non-jam condition indicates that the media 114 is traversing along the media path 116. Thereafter, the processor 402 may be configured to repeat the step 1106.

However, if at step 1204, the media jam detection unit 414 determines that the one or more current characteristics of the input signal satisfy the first transmissivity/reflectivity threshold, the media jam detection unit 414 may perform the step 1208. At step 1208, the printer 100 includes means such as, the control system 208, the processor 402, the media jam detection unit 414, and/or the like, for determining whether a predefined criteria is satisfied. In some examples, the predefined criteria may correspond to a condition, which when satisfied, is indicative of the media jam condition. In an example embodiment, the predefined criteria may correspond to a predetermined time period getting elapsed. In an example embodiment, the predetermined time period may correspond to a time duration for which if the measure of the one or more current characteristics of the input signal (received in the step 1104) satisfy the first transmissivity/reflectivity threshold, the media jam detection unit 414 detects the media jam condition.

Therefore, in an implementation where the predefined criteria corresponds to the predetermined time period getting elapsed, at step 1208, the media jam detection unit 414 may be configured to determine whether the predetermined time period has elapsed.

If the media jam detection unit 414 determines, at the step 1208, that the predetermined time period has not elapsed, the media jam detection unit 414 may be configured to repeat the step 1106. However, if the media jam detection unit 414 determines that the predetermined time period has elapsed, the media jam detection unit 414 may be configured to perform the step 1210. At step 1210, the printer 100 includes means such as, the control system 208, the processor 402, the media jam detection unit 414, and/or the like, for determining that the media jam condition has occurred.

In another implementation, the predetermined criteria may correspond to a jam count exceeding a count threshold. In an example embodiment, the jam count may correspond to a number of times the media jam detection unit 414 has determined the one or more current characteristics to identified the media jam condition. Further, the count threshold may correspond to a maximum jam count beyond which the media jam detection unit 414 may detect the media jam condition. In an example embodiment, when the predefined criteria corresponds to the jam count exceeding the count threshold, the media jam detection unit 414 may be configured to increment in the jam count by one, in an instance in which the one or more current characteristics of the input signal exceeds the first transmissivity/reflectivity threshold. Thereafter, at 1208, the media jam detection unit 414 may be configured to determine whether the jam count is greater than or equal to the count threshold. If the media jam detection unit 414 determines that the jam count exceeds the count threshold, the media jam detection unit 414 may determine that the predefined criteria is satisfied. Accordingly, the media jam detection unit 414 may be configured to perform the step 1210. However, if the media jam detection unit 414 determines that the jam count has not exceeded the count threshold, the media jam detection unit 414 may determine that the predefined criteria has not satisfied. Accordingly, the media jam detection unit 414 may be configured to perform the step 1106.

As described in FIG. 12, the media jam condition is detected based on the value of the first transmissivity/reflectivity threshold. For example, the media jam detection unit 414 detects the media jam condition when the current amplitude of the input signal is less than the first amplitude threshold. Therefore, the sensitivity to detect the media jam condition is dependent on the value of the first transmissivity/reflectivity threshold. If the value of the first transmissivity/reflectivity threshold is altered, as is described supra in FIG. 10, the sensitivity to detect the media jam condition also changes. For example, the value of the first amplitude threshold is 2.5V and the value of the altered first amplitude threshold is 5V. Assuming that the value of the current amplitude of the input signal is 3V, the media jam detection unit 414 may detect the media jam condition if the altered first amplitude threshold is 5V is used as the first transmissivity/reflectivity threshold. Had the first amplitude threshold been used as the first transmissivity/reflectivity threshold, the media jam detection unit 414 may not have detected the media jam condition. Such altering of the first transmissivity/reflectivity threshold directly effects the efficiency of the media jam detection unit 414 to detect the media jam condition. For instance, the media jam detection unit 414 is able to detect the media jam condition quickly, when the altered first amplitude threshold is being used as the first transmissivity/reflectivity threshold, in comparison to detecting the media jam condition when the first amplitude threshold is being used as the first transmissivity/reflectivity threshold.

Referring back to FIG. 11, at step 1110, the printer 100 includes means such as, the control system 208, the processor 402, the media jam detection unit 414, and/or the like, for generating a notification indicating the media jam condition. In an example embodiment, the notification may correspond to a switching ON an LED positioned on the housing of the printer 100. In alternate embodiment, the notification may correspond to an audio notification in which the media jam detection unit 414 may be configured to generate an audio signal to indicate the media jam condition. Further, in such scenario, the printer 100 may include an audio output device such as a speaker. In yet another embodiment, the media jam detection unit 414 may be configured to transmit the notification to the computing device communicatively coupled to the printer 100. On the computing device, the notification may be displayed on a display screen.

Figure 13:
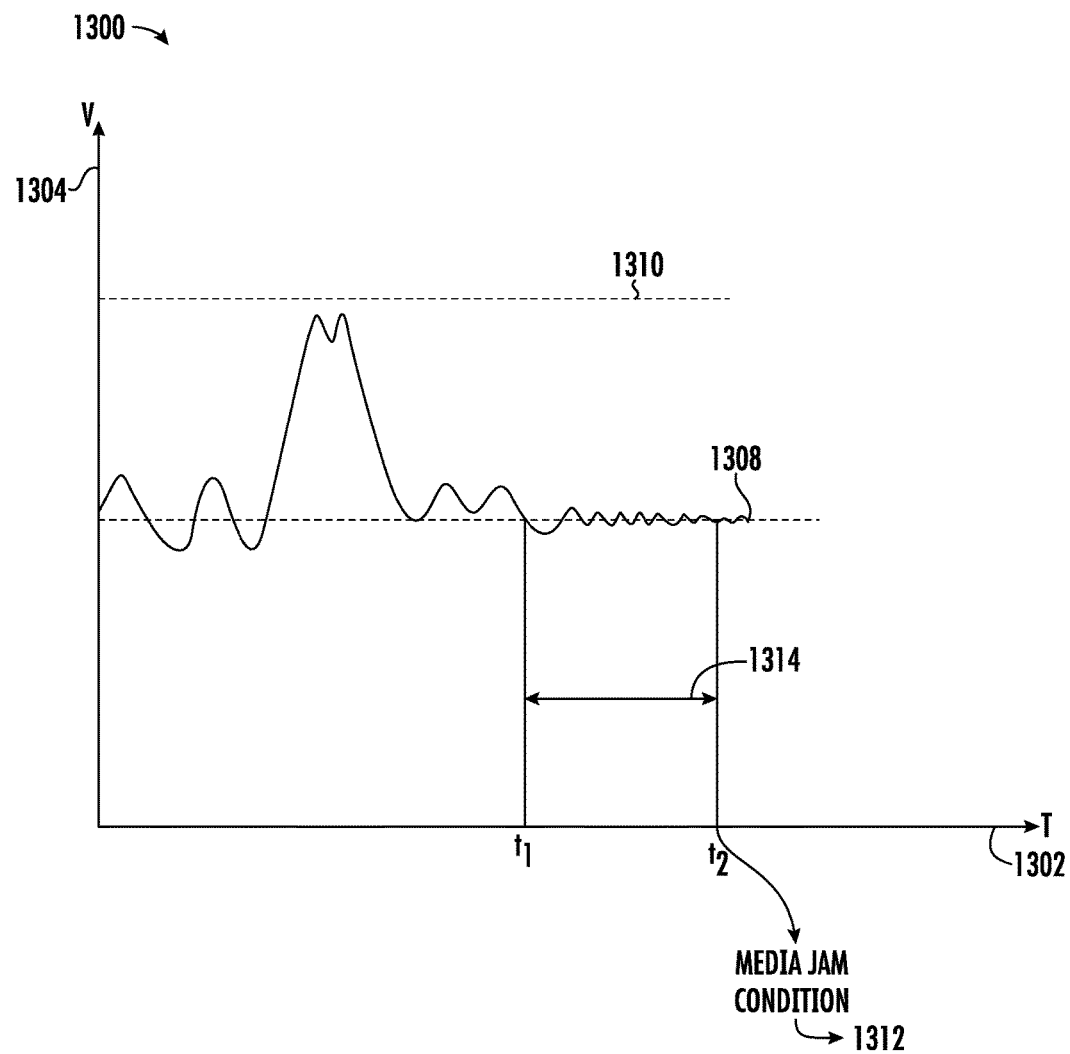
FIG. 13 illustrates a graphical representation of an example input signal received while the printer operates in a printing mode, according to one or more embodiments described herein.

FIG. 13 illustrates graphical representation 1300 of an example input signal received while the printer 100 operates in the printing mode, according to one or more embodiments described herein.

The graphical representation 1300 includes an X-axis 1302 and a Y-axis 1304. The Y-axis 1304 represents the voltage of the input signal received while the printer 100 operates in the printing mode. Further, the Y-axis 1304 represents the time during which the printer 100 operates in the printing mode.

Further, the graphical representation 1300 depicts a curve 1306 corresponding to the input signal. Additionally, the graphical representation 1300 depicts the first line 1308 and a second line 1310. The first line 1308 indicates the first amplitude threshold and the second line 1310 depicts the second amplitude threshold. It can be observed that the amplitude of the input signal (e.g., depicted by the curve 1306) varies between the first amplitude threshold (e.g., depicted by the first line 1308) and the second amplitude threshold (e.g., depicted by the second line 1310) till the time instant $t_1$. Post time instant $t_1$ the amplitude of the input signal remains below the first amplitude threshold (e.g., depicted by the first line 1308). Further, it can be observed that at the time instant $t_2$ the media jam condition is detected (e.g., depicted by 1312). In an example embodiment, the time duration between the time instant $t_1$ and $t_2$ corresponds to the predetermined time period (e.g., depicted by 1314).

In some example embodiments, certain ones of the operations herein may be modified or further amplified as described below. Moreover, in some embodiments additional optional operations may also be included. It should be appreciated that each of the modifications, optional additions or amplifications described herein may be included with the operations herein either alone or in combination with any others among the features described herein.

The foregoing method descriptions and the process flow diagrams are provided merely as illustrative examples and are not intended to require or imply that the steps of the various embodiments must be performed in the order presented. As will be appreciated by one of skill in the art the order of steps in the foregoing embodiments may be performed in any order. Words such as "thereafter," "then," "next," etc. are not intended to limit the order of the steps; these words are simply used to guide the reader through the description of the methods. Further, any reference to claim elements in the singular, for example, using the articles "a," "an" or "the" is not to be construed as limiting the element to the singular.

The hardware used to implement the various illustrative logics, logical blocks, modules, and circuits described in connection with the aspects disclosed herein may include a general purpose processor, a digital signal processor (DSP), a special-purpose processor such as an application specific integrated circuit (ASIC) or a field programmable gate array (FPGA), a programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively or in addition, some steps or methods may be performed by circuitry that is specific to a given function.

In one or more example embodiments, the functions described herein may be implemented by special-purpose hardware or a combination of hardware programmed by firmware or other software. In implementations relying on firmware or other software, the functions may be performed as a result of execution of one or more instructions stored on one or more non-transitory computer-readable media and/or one or more non-transitory processor-readable media. These instructions may be embodied by one or more processor-executable software modules that reside on the one or more non-transitory computer-readable or processor-readable storage media. Non-transitory computer-readable or processor-readable storage media may in this regard comprise any storage media that may be accessed by a computer or a processor. By way of example but not limitation, such non-transitory computer-readable or processor-readable media may include RAM, ROM, EEPROM, FLASH memory, disk storage, magnetic storage devices, or the like. Disk storage, as used herein, includes compact disc (CD), laser disc, optical disc, digital versatile disc (DVD), floppy disk, and Blu-ray Disc™, or other storage devices that store data magnetically or optically with lasers. Combinations of the above types of media are also included within the scope of the terms non-transitory computer-readable and processor-readable media. Additionally, any combination of instructions stored on the one or more non-transitory processor-readable or computer-readable media may be referred to herein as a computer program product.

Many modifications and other embodiments of the inventions set forth herein will come to mind to one skilled in the art to which these inventions pertain having the benefit of teachings presented in the foregoing descriptions and the associated drawings. Although the figures only show certain components of the apparatus and systems described herein, it is understood that various other components may be used in conjunction with the supply management system. Therefore, it is to be understood that the inventions are not to be limited to the specific embodiments disclosed and that modifications and other embodiments are intended to be included within the scope of the appended claims. Moreover, the steps in the method described above may not necessarily occur in the order depicted in the accompanying diagrams, and in some cases one or more of the steps depicted may occur substantially simultaneously, or additional steps may be involved. Although specific terms are employed herein, they are used in a generic and descriptive sense only and not for purposes of limitation.

What is claimed is:

1. A method for detecting a media jam condition in a thermal printer, the method comprising:
   receiving, by a processor, an input signal from a media sensor, wherein the input signal is indicative of a measure of a media transmissivity/reflectivity of a media, wherein content is printed on the media;
   operating, by the processor, the thermal printer in a calibration mode, wherein operating the thermal printer in the calibration mode comprises:
      halting, by the processor, a traversal of the media such that the media is stationary with respect to a print head in the thermal printer, wherein the print head is configured to print on the media;
      analyzing, by the processor, the input signal received while the traversal of the media is halted, to determine one or more characteristics of the input signal; and
      determining, by the processor, a first transmissivity/reflectivity threshold based on the one or more characteristics of the input signal received during the calibration mode; and
   operating, by the processor, the thermal printer in a printing mode, wherein operating the thermal printer in the printing mode comprises:
      causing, by the processor, traversal of the media with respect to the print head in the thermal printer to perform a print operation;
      determining, by the processor, one or more current characteristics of the input signal received while the thermal printer operates in the printing mode; and
      detecting, by the processor, the media jam condition in an instance in which a measure of the one or more current characteristics of the input signal, received while the thermal printer operates in the printing mode, is satisfy the first transmissivity/reflectivity threshold.

2. The method of claim 1, wherein the one or more characteristics comprise at least one of an amplitude of the input signal or a frequency of the input signal.

3. The method of claim 1, wherein the one or more current characteristics of the input signal comprise at least one of a current measure of an amplitude of the input signal or a current measure of a frequency of the input signal.

4. The method of claim 1, wherein the first transmissivity/reflectivity threshold comprises at least one of a first amplitude threshold, a first amplitude variation measurement threshold, or a first frequency threshold.

5. The method of claim 4, wherein the media jam condition is detected when the measure of the one or more current characteristics of the input signal, received while the thermal printer operates in the printing mode, is less than or equal to the first amplitude threshold and is greater than or equal to the first frequency threshold, for a predetermined time period.

6. The method of claim 4, further comprising determining a current amplitude variation measurement based on a current amplitude of the input signal and a previous amplitude of the input signal, wherein the media jam condition is detected in an instance in which the current amplitude variation measurement is less than or equal to the first amplitude variation measurement threshold, for a predetermined time period.

7. The method of claim 4 further comprising incrementing a jam count in an instance in which the measure of the one or more current characteristics of the input signal, received while the thermal printer operates in the printing mode, is less than or equal to the first amplitude threshold and is greater than or equal to the first frequency threshold.

8. The method of claim 7 further comprising detecting the media jam condition when the jam count exceeds a count threshold.

9. The method of claim 1 further comprising generating a notification indicative of the media jam condition.

10. The method of claim 1, wherein operating the thermal printer in the calibration mode further comprises:
   causing, by the processor, the media to move with respect to the print head;
   receiving, by the processor, the input signal from the media sensor, while the media traverses with respect to the print head; and
   determining, by the processor, a second transmissivity/reflectivity threshold based on one or more characteristics of the input signal, received while the media traverses with respect to the print head, wherein the second transmissivity/reflectivity threshold comprise a second amplitude threshold and a second frequency threshold.

11. The method of claim 10 further comprising detecting a non-jam condition when the measure of the one or more current characteristics of the input signal, received while the thermal printer operates in the printing mode, is between the first transmissivity/reflectivity threshold and the second transmissivity/reflectivity threshold.

12. A thermal printer comprising:
   a print head configured to print on a media;
   a media sensor positioned within the thermal printer, wherein the media sensor is configured to generate an input signal indicative of a measure of a media transmissivity/reflectivity;
   a processor configured to:
      receive the input signal from the media sensor, while the media is stationary with respect to the print head,
      analyze the input signal received while the traversal of the media is stationary with respect to the print head, to determine one or more characteristics of the input signal
      determine a first transmissivity/reflectivity threshold based on the one or more characteristics of the input signal received while the media is stationary with respect to the print head,
      receive the input signal from the media sensor, while the media traverses with respect to the print head,
      determine one or more current characteristics of the input signal while the media traverses with respect to the print head, and
      detect a media jam condition in an instance in which a measure of the one or more current characteristics of the input signal, received while the media traverses with respect to the print head, is satisfies the first transmissivity/reflectivity threshold.

13. The thermal printer of claim 12, wherein the one or more current characteristics of the input signal comprise at least one of a current measure of an amplitude of the input signal or a current measure of a frequency of the input signal.

14. The thermal printer of claim 12, wherein the first transmissivity/reflectivity threshold comprises at least one of a first amplitude threshold or a first frequency threshold.

15. The thermal printer of claim 12, wherein the processor is further configured to operate the thermal printer in a calibration mode, wherein, in the calibration mode, the processor is configured to halt a traversal of the media such that the media is stationary with respect to the print head, wherein the first transmissivity/reflectivity threshold is determined during the calibration mode.

16. The thermal printer of claim 15, wherein, during the calibration mode, the processor is further configured to:
cause the media to move with respect to the print head;
receive the input signal from the media sensor, while the media traverses with respect to the print head; and
determine a second transmissivity/reflectivity threshold based on one or more characteristics of the input signal, received while the media traverses with respect to the print head, wherein the second transmissivity/reflectivity threshold comprise at least one of a second amplitude threshold or a second frequency threshold.

17. The thermal printer of claim 16, wherein the processor is configured to detect a non-jam condition when the measure of the one or more current characteristics of the input signal, received while the media traverses with respect to the print head, is between the first transmissivity/reflectivity threshold and the second transmissivity/reflectivity threshold.

18. The thermal printer of claim 12, wherein the processor is further configured to operate the thermal printer in a printing mode, wherein the media jam condition is detected during the printing mode.

19. The thermal printer of claim 12, wherein the processor is further configured to operate the thermal printer in an idle mode, wherein, in the idle mode, the media is stationary with respect to the print head, wherein the first transmissivity/reflectivity threshold is determined during the idle mode.

20. The thermal printer of claim 12, wherein the one or more characteristics comprises a measure of an amplitude of the input signal, and/or a measure a frequency of the input signal.

21. The thermal printer of claim 12, wherein the media jam condition is detected when the measure of the one or more current characteristics of the input signal, received while the media traverses with respect to the print head, satisfies the first transmissivity/reflectivity threshold for a predetermined time period.

22. The thermal printer of claim 12, wherein the processor is further configured to generate a notification indicative of the media jam condition.

\* \* \* \* \*